United States Patent [19]
Stein et al.

[11] Patent Number: 5,854,223
[45] Date of Patent: Dec. 29, 1998

[54] S-DC28 AS AN ANTIRESTENOSIS AGENT AFTER BALLOON INJURY

[75] Inventors: Cy Stein, New City; LeRoy Rabbani, New York, both of N.Y.

[73] Assignee: The Trustees of Columbia University in the City of New York, New York, N.Y.

[21] Appl. No.: 678,234

[22] Filed: Jul. 11, 1996

[51] Int. Cl.$^6$ .................................................. A61K 48/00
[52] U.S. Cl. ............................................ 514/44; 536/24.5
[58] Field of Search .............................. 514/44; 536/24.5

[56] References Cited

PUBLICATIONS

Jarvis et al., RNA, 2:419–428, 1996.
Bennett, M. R., et al., "Inhibition of Vascular Smooth Muscle Cell Proliferation In Vitro and In Vivo by C–MYC Antisense Oligodeoxynucleotides", *J. Clin. Invest.* (1994) 93(2): 820–828 (Exhibit B).
Biro, S., et al., "Inhibitory effects of antisense oligodeoxynucleotides targeting c–myc mRNA on smooth muscle cell proliferation and migration", *Proc. Natl. Acad. Sci. U.S.A.* (1993) 90(2): 654–658 (Exhibit C).
Brown, K. E., et al., "Expression of the c–myb Proto–oncogene in Bovine Vascular Smooth Muscle Cells", *J. Biol. Chem.* (1992) 267(7): 4625–4630 (Exhibit D).
Burgess, T.L., "The antiproliferation activity of c–myb and c–myc antisense oligonucleotides in smooth muscle cells is caused by a nonantisense mechanism", *Proc. Natl. Acad. Sci. U.S.A.* (1995) 92(9): 4051–4055 (Exhibit E).
Ebbecke, M., et al., "Antiproliferative effects of c–myc antisense oligonucleotide on human arterial smooth muscle cells", *Basic Res. Cardiol.* (1992) 87(6): 585–591 (Exhibit F).
Morishita, R., et al., "Pharmacokinetics of antisense oligodeoxyribonucleotides (cyclin $B_1$ and CDC 2 kinase) in the vessel wall in vivo: enhanced therapeutic utility for restenosis by HVJ–liposome delivery", *Gene* (1994) 149: 13–19 (Exhibit G).

Shi, Y., et al., "Downregulation of c–myc Expression by Antisense Oligonucleotides Inhibits Proliferation of Human Smooth Muscle Cells", *Circulation* (1993) 88(3): 1190–1195 (Exhibit H).
Shi, Y., et al., "Transcatheter Delivery of c–myc Antisense Oligomers Reduces Neointimal Formation in a Porcine Model of Coronary Artery Balloon Injury", *Circulation Research*, 90(2): 944–951 (Exhibit I).
Simons, M. and Rosenberg, R.D., "Antisense Nonmuscle Myosin Heavy Chain and c–myb Oligonucleotides Suppress Smooth Muscle Cell Proliferation In Vitro", *Circ. Res.* (1992) 70(4): 835–843 (Exhibit J).
Simons, M., et al., "Antisense c–myb oligonucleotides inhibit intimal arterial smooth muscle cell accumulation in vivo", *Nature* (1992) 359: 67–70 (Exhibit K).
Stein, C.A. and Cheng, Y.C., "Antisense Oligonucleotides as Therapeutic Agents–Is the Bullet Really Magical?", *Science* (1993) 261: 1004–1011 (Exhibit L).
Villa, A., et al, "Effects of Antisense c–myb Oligonucleotides on Vascular Smooth Muscle Cell Proliferation and Response to Vessel Wall Injury", *Circulation Research* (1995) 76(4): 505–513 (Exhibit M).

*Primary Examiner*—Scott W. Houtteman
*Attorney, Agent, or Firm*—John P. White; Cooper & Dunham LLP

[57] ABSTRACT

This invention provides methods of inhibiting proliferation, migration and heterotypic adhesion of vascular smooth muscle cells which comprise contacting the vascular smooth muscle cells with an amount of a phosphorothioate oligonucleotide moiety effective to inhibit the proliferation, migration or heterotypic adhesion of the vascular smooth muscle cells. This invention provides methods of inhibiting neointimal formation after balloon injury, percutaneous transluminal coronary angioplasty restenosis, and coronary artery stent restenosis in a subject which comprise administering to the subject an amount of a phosphorothioate oligonucleotide moiety effective to inhibit neointimal formation, percutaneous transluminal coronary angioplasty restenosis, or coronary artery stent restenosis in the subject. This invention further provides pharmaceutical compositions effective for treating the conditions recited above.

15 Claims, 17 Drawing Sheets

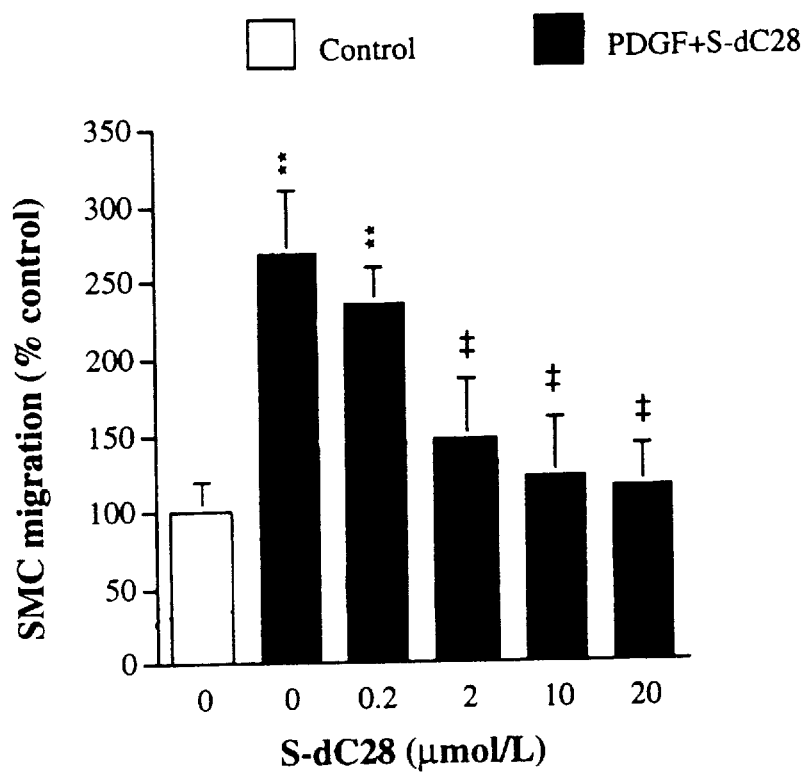

S-DC28 AS AN ANTIRESTENOSIS AGENT AFTER BALLOON INJURY

This invention was made with support under Grant Nos. 02578 and 60639 from the National Institutes of Health, U.S. Department of Health and Human Services. Accordingly, the United States Government has certain rights in the invention.

This application claims the benefit of U.S. Provisional Application No. 60/005,276, filed Oct. 6, 1995, the contents of which are hereby incorporated by reference into the present application.

Throughout this application, various publications are referenced by numerals in brackets. Full citations for these publications may be found listed at the end of the specification immediately preceding the claims. The disclosures of these publications in their entireties are hereby incorporated by reference into this application in order to more fully describe the state of the art as known to those skilled therein as of the date of the invention described and claimed herein.

BACKGROUND OF THE INVENTION

Restenosis after percutaneous transluminal coronary angioplasty remains a vexing problem, occurring in 30% to 50% of patients within three to six months of the procedure [1]. Moreover, a plethora of different pharmacological strategies to prevent restenosis have proved to be profoundly disappointing in this regard [2]. Vascular smooth muscle cells (SMC) have been implicated in the etiology of restenosis characterized by phenotypic transition from a contractile to synthetic state associated with SMC proliferation and SMC migration from the media to the intima [3,4].

Major emphasis has centered on developing sequence-specific antisense strategies to inhibit SMC proliferation and restenosis by employing phosphorothioate oligonucleotides (PS oligos) targeted against various proto-oncogenes involved in cellular proliferation [5]. PS oligos are antisense (sequence-specific), nuclease resistant, isoelectronic congeners of phosphodiester oligonucleotides that are soluble in aqueous solutions and engage in Watson-Crick base pair hybridization [6]. Indeed, several different groups have demonstrated antisense inhibition of in vitro SMC proliferation utilizing oligos complementary to the proto-oncogenes c-myb and c-myc [4,7–12]. Moreover, PS oligos appear to have induced inhibition of restenosis after balloon injury in both the rat carotid and porcine models [7,8,13].

Recently, the underlying mechanism of inhibition of both in vitro SMC proliferation and in vivo neointimal hyperplasia after balloon injury by the aforementioned PS oligos complementary to c-myb and c-myc has been challenged. One study suggests that the inhibitory effects of these oligos of SMC proliferation in vitro and in vivo is not the result of a hybridization-dependent antisense mechanism, but is the consequence of an aptamer effect consisting of four consecutive guanosine (G-quartet) residues, present in both the antisense c-myb and c-myc oligos [14]. Thus, the consecutive G-quartet sequence is necessary for the sequence-selective protein binding but not antisense inhibitory properties of these oligos [14]. Another study has provided further support for the lack of specificity and inconsistency in the anti-proliferative effects of these oligos both in vitro and in vivo [5]. Once again, a G-quartet residue sequence appeared to be necessary for inhibition of SMC proliferation [5]. Furthermore, rat carotid neointimal hyperplasia after balloon injury was equivalent for antisense c-myb and sense c-myb [5]. In vitro smooth muscle cell proliferation was inhibited by both sense and anti-sense c-myb oligos containing the consecutive G-quartet sequences [5].

Phosphorothioate oligonucleotides (PS oligos) have more recently been demonstrated to possess additional properties which may be germane to their SMC antiproliferative effects. Indeed, PS oligos have been demonstrated to bind directly to various heparin-binding growth factors such as bFGF (basic fibroblast growth factor) and PDGF (platelet-derived growth factor) [15]. Given the confusion surrounding the mechanism of action of the SMC antiproliferative effects of the PS oligos and the recent demonstration of non-antisense, non-sequence specific effects of the PS oligos, it was hypothesized that the inhibitory effects of the PS oligos on SMC proliferation in vitro and neointimal hyperplasia after balloon injury in vivo are the direct result of non-G-quartet, non-sequence specific inhibition by the PS oligos. Therefore, in this study, in order to determine whether PS oligos manifest non-G-quartet, non-sequence specific anti-proliferative effects on SMC in vitro and in vivo, the effects of S-dC28, a 28-mer phosphorothioate cytidine homopolymer which lacks a contiguous G-quartet residue, were examined. It was demonstrated that the PS oligo, S-dC28, exerts potent non-G-quartet, non-sequence specific inhibitory effects on in vitro human aortic SMC proliferation induced by several mitogens, in vitro human aortic SMC migration, and in vivo neointimal formation after balloon injury in the rat carotid artery model.

The ability of PS oligos to inhibit vascular SMC adhesion in vitro in a non-G-quartet, non-sequence specific manner and if these effects may be modulated by ECM proteins such as laminin and fibronectin was also studied. Furthermore, it was demonstrated that S-dC28 inhibits vascular SMC adhesion in vitro by a non-G-quartet, non-sequence specific mechanism, and that this inhibition can be attenuated by fibronectin, laminin, or serum.

SUMMARY OF THE INVENTION

This invention provides a method of inhibiting proliferation of vascular smooth muscle cells which comprises contacting the vascular smooth muscle cells with an amount of a phosphorothioate oligonucleotide moiety effective to inhibit proliferation of the vascular smooth muscle cells.

This invention further provides a method of inhibiting migration of vascular smooth muscle cells which comprises contacting the vascular smooth muscle cells with an amount of a phosphorothioate oligonucleotide moiety effective to inhibit migration of the vascular smooth muscle cells.

This invention further provides a method of inhibiting neointimal formation after balloon injury in a subject which comprises administering to the subject an amount of a phosphorothioate oligonucleotide moiety effective to inhibit neointimal formation.

This invention provides a method of inhibiting heterotypic adhesion of vascular smooth muscle cells which comprises contacting the vascular smooth muscle cells with an amount of a phosphorothioate oligonucleotide moiety effective to inhibit heterotypic adhesion of the vascular smooth muscle cells.

This invention provides a method of inhibiting percutaneous transluminal coronary angioplasty restenosis in a subject which comprises administering to the subject an amount of a phosphorothioate oligonucleotide moiety effective to inhibit percutaneous transluminal coronary angioplasty restenosis.

This invention further provides a method of inhibiting coronary artery stent restenosis in a subject which comprises administering to the subject an amount of a phosphorothioate oligonucleotide moiety effective to inhibit coronary artery stent restenosis.

Lastly, this invention provides pharmaceutical compositions effective for treating the conditions recited above.

BRIEF DESCRIPTION OF THE FIGURES

FIG. 1A: Effects of S-dC28 on human aortic SMC proliferation stimulated by PDGF. Growth-arrested human aortic SMC were incubated with vehicle alone, PDGF 100 (ng/ml) alone, or PDGF (100 ng/ml) in combination with various doses of S-dC28 for 48 hours at 37° C. in a humidified 5% $CO_2$ atmosphere. SMC were then trypsinized and cell numbers immediately determined by triplicate counts with a Coulter Counter. Values are mean±SD (n=7). (**$p<0.01$ relative to control SMC cultured in media alone; ‡$p<0.01$ compared to the PDGF alone group).

FIG. 1B: Effects of S-dC28 on human aortic SMC proliferation stimulated by bFGF. Growth-arrested human aortic SMC were incubated with vehicle alone, bFGF (10 ng/ml) alone, or bFGF (10 ng/ml) in combination with various doses of S-dC28 for 48 hours at 37° C. in a humidified 5% $CO_2$ atmosphere. SMC were then trypsinized and cell numbers immediately determined by triplicate counts with a Coulter Counter. Values are mean±SD (n=6). (**$p<0.01$ relative to control SMC cultured in media alone; ‡$p<0.01$ compared to the bFGF alone group).

FIG. 1C: Effects of S-dC28 on human aortic SMC proliferation stimulated by EGF. Growth-arrested human aortic SMC were incubated with vehicle alone, EGF (10 ng/ml) alone, or EGF (10 ng/ml) in combination with various doses of S-dC28 for 48 hours at 37° C. in a humidified 5% $CO_2$ atmosphere. SMC were then trypsinized and cell numbers immediately determined by triplicate counts with a Coulter Counter. Values are mean±SD (n=6). (**$p<0.01$ relative to control SMC cultured in media alone; ‡$p<0.01$ compared to the EGF alone group).

FIG. 1D: Effects of S-dC28 on human aortic SMC proliferation stimulated by 10% FBS. Growth-arrested human aortic SMC were incubated with vehicle alone, 10% FBS alone, or 10% FBS in combination with various doses of S-dC28 for 48 hours at 37° C. in a humidified 5% $CO_2$ atmosphere. SMC were then trypsinzied and cell numbers immediately determined by triplicate counts with a Coulter Counter. Values are mean ± SD (n=6). (**$p<0.0l$ relative to control SMC cultured in media alone; ‡$p<0.01$ compared to the 10% FBS alone group).

FIG. 3: Effects of S-dC28 on SMC Migration. SMC migration studies were performed using a modified micro Boyden Chamber. Human aortic SMC ($5\times10^5$/ml) were added into the upper chamber of the transwell, while vehicle alone, PDGF 100 (ng/ml) alone, or PDGF (100 ng/ml) in combination with various doses of S-dC28 were added to the lower chamber. SMC migration was determined using the Coulter Counter after a 48 hour incubation at 37° C. in a humidified 5% $CO_2$ atmosphere. Migration activity was determined by the ratio of cell number of triplicate counts in the upper and lower chambers of the apparatus. Values are mean±SD (n=6) (**$p<0.01$ relative to control SMC cultured in media alone; ‡$p<0.01$ compared to the PDGF alone group).

FIG. 8A. SMC incubated with 2% bovine albumin for 6 hours. FIG. 8B. SMC incubated with 2% bovine albumin for 16 hours. FIG. 8C. SMC incubated with 2% bovine albumin and SMC treated with S-dC28 20 $\mu$M for 6 hours. FIG. 8D. SMC incubated with 2% bovine albumin and SMC treated with S-dC28 20 $\mu$M for 16 hours.

DETAILED DESCRIPTION OF THE INVENTION

Figure 1A:
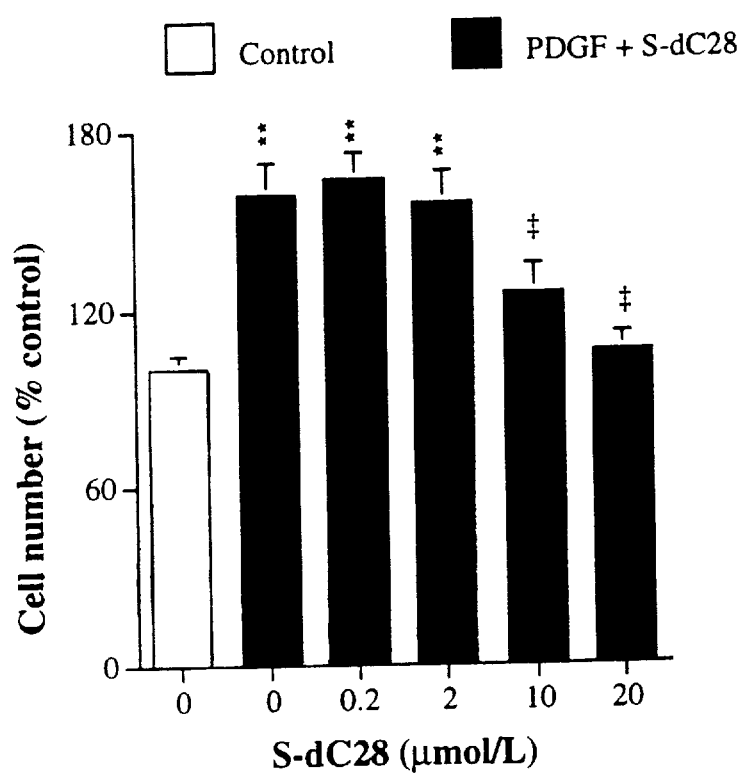
FIGS. 1A–1D

The present invention provides a method of inhibiting proliferation of vascular smooth muscle cells which comprises contacting the vascular smooth muscle cells with an amount of a phosphorothioate oligonucleotide moiety effective to inhibit proliferation of the vascular smooth muscle cells.

As used herein, the phrase "an amount of a phosphorothioate oligonucleotide moiety effective to inhibit proliferation of the vascular smooth muscle cells" means that amount of a phosphorothioate oligonucleotide moiety which is effective in inhibiting the proliferation of vascular smooth muscle cells. The amount of phosphorothioate oligonucleotide moiety needed to practice the claimed method varies with the length of the oligonucleotide and the means by which the contact occurs. For example, if the contact occurs in vitro and a 28 base oligonucleotide is utilized, the preferred effective amount is in the range of 0.01–50 $\mu$M.

Further, as is known to those of ordinary skill in the art effective amounts vary with the type of therapeutic agent. It is known to those of ordinary skill in the art how to determine an effective amount of a suitable therapeutic agent.

The present invention further provides a method of inhibiting migration of vascular smooth muscle cells which comprises contacting the vascular smooth muscle cells with an amount of a phosphorothioate oligonucleotide moiety effective to inhibit migration of the vascular smooth muscle cells.

As used herein, the phrase "an amount of a phosphorothioate oligonucleotide moiety effective to inhibit migration of the vascular smooth muscle cells" means that amount of a phosphorothioate oligonucleotide moiety which is effective in inhibiting the migration of vascular smooth muscle cells. The amount of phosphorothioate oligonucleotide moiety needed to practice the claimed method varies with the length of the oligonucleotide. For example, if the contact occurs in vitro and a 28 base oligonucleotide is utilized, the preferred effective amount is in the range of 0.01–50 $\mu$M.

Further, as is known to those of ordinary skill in the art effective amounts vary with the type of therapeutic agent. It is known to those of ordinary skill in the art how to determine an effective amount of a suitable therapeutic agent.

The present invention further provides a method of inhibiting neointimal formation after balloon injury in a subject which comprises administering to the subject an amount of a phosphorothioate oligonucleotide moiety effective to inhibit neointimal formation.

As used herein, the phrase "an amount of a phosphorothioate oligonucleotide moiety effective to inhibit neointimal formation" means that amount of a phosphorothioate oligonucleotide moiety which is effective in inhibiting neointimal formation. The amount of the phosphorothioate oligonucleotide moiety effective to inhibit neointimal formation may be in the range of 0.001–300 $\mu$M. The amount of phosphorothioate oligonucleotide moiety needed to practice the claimed method varies with the length of the oligonucleotide.

Further, as is known to those of ordinary skill in the art effective amounts vary with the type of therapeutic agent. It is known to those of ordinary skill in the art how to determine an effective amount of a suitable therapeutic agent.

As used herein "neointimal formation" refers to the formation of a layer of smooth muscle cells in the intima. After balloon injury smooth muscle cells from the media, which are not normally present in the intima, proliferate and migrate to the intima forming a layer which obscures blood flow.

As used herein, inhibition of neointimal formation refers to the inhibition of migration and proliferation of smooth muscle cells so as to prevent neointimal formation and complications arising therefrom.

The subject may be a mammal or more specifically a human, dog, cat, rodent, or monkey.

The present invention further provides a method of inhibiting percutaneous transluminal coronary angioplasty restenosis in a subject which comprises administering to the subject an amount of a phosphorothioate oligonucleotide moiety effective to inhibit percutaneous transluminal coronary angioplasty restenosis.

As used herein, the phrase "an amount of a phosphorothioate oligonucleotide moiety effective to inhibit percutaneous transluminal coronary angioplasty restenosis" means that amount of a phosphorothioate oligonucleotide moiety which is effective in inhibiting the percutaneous transluminal coronary angioplasty restenosis. The amount of the phosphorothioate oligonucleotide moiety effective to inhibit percutaneous transluminal coronary angioplasty restenosis may be in the range of 0.001–300 $\mu$M. The amount of phosphorothioate oligonucleotide moiety needed to practice the claimed method varies with the length of the oligonucleotide.

Further, as is known to those of ordinary skill in the art effective amounts vary with the type of therapeutic agent. It is known to those of ordinary skill in the art how to determine an effective amount of a suitable therapeutic agent.

As used herein "percutaneous transluminal coronary angioplasty restenosis" refers to the return of blockage in the artery due to neointimal formation of a layer of smooth muscle cells in the intima after balloon injury. After balloon injury smooth muscle cells from the media, which are not normally present in the intima, proliferate and migrate to the intima forming a layer which obscures blood flow.

As used herein, inhibition of "percutaneous transluminal coronary angioplasty restenosis" refers to the inhibition of migration and proliferation of smooth muscle cells so as to prevent neointimal formation and the return of blockage in the artery at the site of the balloon injury.

The subject may be a mammal or more specifically a human, dog, cat, rodent, or monkey.

The present invention further provides a method of inhibiting coronary artery stent restenosis in a subject which comprises administering to the subject an amount of a phosphorothioate oligonucleotide moiety effective to inhibit coronary artery stent restenosis.

As used herein, the phrase "an amount of a phosphorothioate oligonucleotide moiety effective to inhibit coronary artery stent restenosis" means that amount of a phosphorothioate oligonucleotide moiety which is effective in inhibiting coronary artery stent restenosis. The amount of the phosphorothioate oligonucleotide moiety effective to inhibit coronary artery stent restenosis may be in the range of 0.001–300 $\mu$M. The amount of phosphorothioate oligonucleotide moiety needed to practice the claimed method varies with the length of the oligonucleotide.

Further, as is known to those of ordinary skill in the art effective amounts vary with the type of therapeutic agent. It is known to those of ordinary skill in the art how to determine an effective amount of a suitable therapeutic agent.

The subject may be a mammal or more specifically a human, dog, cat, rodent, or monkey.

As used herein "coronary artery stent restenosis" refers to the return of blockage in the artery due to neointimal formation of a layer of smooth muscle cells in the intima after balloon injury at the site where the stent was inserted. After balloon injury smooth muscle cells from the media, which are not normally present in the intima, proliferate and migrate to the intima forming a layer which obscures blood flow.

As used herein, inhibition of "coronary artery stent restenosis" refers to the inhibition of migration and proliferation of smooth muscle cells so as to prevent neointimal formation and the return of blockage in the artery at the site where the stent was inserted.

The present invention further provides a method of inhibiting heterotypic adhesion of vascular smooth muscle cells which comprises contacting the vascular smooth muscle cells with an amount of a phosphorothioate oligonucleotide moiety effective to inhibit heterotypic adhesion of vascular smooth muscle cells.

As used herein, the phrase "an amount of a phosphorothioate oligonucleotide moiety effective to inhibit heterotypic adhesion of vascular smooth muscle cells" means that amount of a phosphorothioate oligonucleotide moiety which is effective in inhibiting heterotypic adhesion of vascular smooth muscle cells. The amount of phosphorothioate oligonucleotide moiety needed to practice the claimed method varies with the length of the oligonucleotide. For example, if the contact occurs in vitro and a 28 base oligonucleotide is utilized, the preferred effective amount is in the range of 0.01–50 $\mu$M.

Further, as is known to those of ordinary skill in the art effective amounts vary with the type of therapeutic agent. It is known to those of ordinary skill in the art how to determine an effective amount of a suitable therapeutic agent.

"Heterotypic adhesion of vascular smooth muscle cells" refers to the adhesion of vascular smooth muscle cells to any variety of cell other than vascular smooth muscle cells. Examples of heterotypic adhesion include, but are not limited to, the adhesion of vascular smooth muscle cells to artery walls and the adhesion of vascular smooth muscle cells to blood cells.

The methods of the present invention may be practiced in vivo or in vitro. If the methods are practiced in vitro, contacting may be effected by incubating the cells with the phosphorothioate oligonucleotide moieties described herein. The concentration of the phosphorothioate oligonucleotide moiety in contact with the cells should be from about 0.01 $\mu$M to about 50 $\mu$M. The contact should occur for about 1 to 72 hours, preferably for about 1 to 48 hours.

In another embodiment of the present invention the stent is coated with a phosphorothioate oligonucleotide moiety prior to insertion. The coating of the stent with the phosphorothioate oligonucleotide moiety inhibits the growth of vascular smooth muscle cells and neointimal formation at the site of the stent.

Oligonucleotides are compounds made up of repeating units of nucleotides. These compounds are also known as chimeric oligonucleotides.

Synthetic oligodeoxynucleotides have been utilized as antisense inhibitors of mRNA translation in vitro and in vivo [37,40,42,46,48]. Antisense oligonucleotides have found widespread application because of their abilities to control and/or inhibit gene expression in a selective manner in cellular systems [38,39,41,43,47,49]. Antisense oligonucleotides bind specifically by hydrogen bonding to complementary nucleic acids, thereby inhibiting the messenger ribonucleic acid (mRNA) from translating a protein molecule. In other words, antisense RNA functions by contacting an mRNA species and inhibiting the production of the protein which the mRNA encodes. The present invention does not proceed via an antisense mechanism.

Phosphorothioate (PS) is an oligodeoxynucleotide in which the sulfur atom replaces one of the non-bridging oxygen atoms in one or more phosphodiester linkage, i.e. an oligonucleotide or oligodeoxynucleotide having one or more phosphorothiodiester linkages. Each phosphorothiodiester linkage can occur as either an Rp or Sp diastereomer. A bridging oxygen atom is an oxygen atom in a phosphodiester linkage of a nucleic acid which joins phosphorous to a sugar.

One or more of the phosphorothiodiester linkages of the phosphorothioate oligonucleotide may be modified by replacing one or both of the two bridging oxygen atoms of the linkage with analogues such as NH—, $CH_2$—, or S—. Other oxygen analogues known in the art may also be used.

Phosphorothioate oligodeoxynucleotides are relatively nuclease resistant water soluble analogs of phosphodiester oligodeoxynucleotides. These molecules are racemic, but still hybridize well to their RNA targets [44].

Further, since many classes of oligodeoxynucleotides [e.g., phosphodiesters (PO) and phosphorothioates (PS)] are polyanions, they cannot passively diffuse through lipophilic cell membranes [45]. However, the majority of oligonucleotide internalization is not due to receptor-mediated endocytosis, but rather results indicate that bulk internalization is predominately from pinocytosis, fluid-phase endocytosis.

Throughout this application, references to specific nucleotides are to nucleotide present on the coding strand of the nucleic acid. The following standard abbreviations are used throughout the specification to indicate specific nucleotides:

C=Cytidine A=Adenosine
T=Thymidine G=Guanosine

Examples of phosphorothioate oligonucleotide moieties include, but are not limited to, a phosphorothioate oligodeoxynucleotide, a phosphorodithioate, a chimeric oligonucleotide, an oligonucleotide homopolymer, an oligonucleotide heteropolymer, or a phosphorothioate oligonucleotide which is further linked to another chemical moiety.

In one embodiment the phosphorothioate oligonucleotide moiety is a chain of cytidine nucleotide sequences. In another embodiment the phosphorothioate oligonucleotide moiety is a chain of adenosine nucleotide sequences. In another embodiment, the phosphorothioate oligonucleotide moiety is a chain of thymidine nucleotide sequences. The most preferred embodiment is the cytidine nucleotide sequence.

The phosphorothioate oligonucleotide may be stereo regular, stereo non-regular or stereo random. A stereo regular phosphorothioate oligonucleotide is a phosphorothioate oligonucleotide in which all the phosphodiester linkages or phosphorothiodiester linkages polarize light in the same direction. Each phosphorous in each linkage may be either an Sp or Rp diastereomer. Phosphorothioate oligonucleotides which are created in an automated synthesizer are stereo random which means that each phosphorous atom in the phosphorothioate oligonucleotide has a 50% chance of being either an Sp or Rp diastereomer.

In one embodiment the phosphorothioate oligonucleotide moiety comprises a phosphorothioate oligonucleotide. In another embodiment, the phosphorothioate oligonucleotide moiety comprises a phosphorothioate oligonucleotide linked to another chemical moiety, such as a cholesteryl moiety, an intercalating agent, a cross-linker, an artificial endonuclease, a lipophilic carrier, a peptide conjugate, or a combination thereof.

A phosphorothioate oligonucleotide may be a homopolymer or a heteropolymer. As used herein a "homopolymer" is a sequence of repeating cytidine, adenosine or thymidine nucleotides or other natural bases thereof. For example, S-dC28 is a phosphorothioate oligonucleotide that is a homopolymer of 28 cytidine nucleotides. A heteropolymer is a sequence of alternating cytidine, guanosine, adenosine, or thymidine nucleotides or other natural bases thereof. For example, S-d(CT)10 is a phosphorothioate oligonucleotide that is a heteropolymer of 20 alternating cytidine and thymidine nucleotides.

In one embodiment the phosphorothioate oligonucleotide is a chain structure of 18–100 nucleotides. In a further embodiment the phosphorothioate oligonucleotide is a chain structure of 28 nucleotides.

In addition, the phosphorothioate oligonucleotide may be substituted or modified in its internucleotide phosphate residue with a thioether, carbamate, carbonate, acetamidate or carboxymethyl ester.

In addition, the phosphorothioate oligonucleotide of the phosphorothioate oligonucleotide moiety may have one or more of its nucleotide bases substituted or modified or replaced so as to be ribose, glucose, sucrose, or galactose or any other sugar. Alternatively, the phosphorothioate oligonucleotide may have one or more of its sugars substituted or modified in its 2' position, i.e. 2'allyl or 2'-O-allyl. An example of a 2'-O-allyl sugar is a 2'-O-methylribonucleotide. Further, the phosphorothioate oligonucleotide may have one or more of its sugars substituted or modified to form an α-anomeric sugar.

In addition, the phosphorothioate oligonucleotide may have one or more of its nucleotide bases substituted or modified. Apart from the bases of adenine, guanine, cytosine, and thymine, other natural bases, such as inosine, deoxyinsosine, hypoxanthine are acceptable in the phosphorothioate oligonucleotide moiety useful in the subject invention. In addition, isosteric purine 2'deoxy-furanoside analogues, 2'-deoxynebularine or 2'deoxyxanthosine, or other purine or pyrimidine analogues may also be used.

The present invention further provides that one or both ends of the phosphorothioate oligonucleotide of the phosphorothioate oligonucleotide moiety may be linked with the following chemical moieties: intercalating agents, such as acridine derivatives; cross-linkers, such as psoralen derivatives, azidophenacyl, proflavin, and azidoproflavin; artificial endonucleases, which comprise those conjugates whose nuclease component is able as such to cleave DNA specifically and nonspecifically, and acquires a specificity by covalent linkage to the oligonucleotide portion, such as metal complexes EDTA-Fe(II), o-phenanthroline-Cu(I), and porphyrin-Fe(II); and lipophilic carriers or peptide conjugates, such as long chain alcohols, phosphate esters, amino or mercapto groups, dyes or nonradioactive markers and polylysine or other polyamines.

Furthermore, one or both ends of the phosphorothioate oligonucleotide moiety may be linked with the following chemical moieties: intercalating agents, such as 2-methoxy-6-chloroacridine, methylphosphonates, methylesters, and aminoalkyls; alkylating oligonucleotides, such as acetyl; artificial endonucleases, such as amino-1-hexanolstaphylococcal nuclease, and alkaline phosphatase; peptide conjugates, such as polylysine; and terminal transferases.

In another embodiment, the phosphorothioate oligonucleotide moiety comprises a phosphorothioate oligonucleotide conjugated to a carbohydrate, sulfated carbohydrate, or glycan. Conjugates may be regarded in such a way as to introduce a specificity into otherwise unspecific DNA binding molecules by covalently linking them to a selectively hybridizing oligonucleotide.

In addition, the phosphorothioate oligonucleotide of the phosphorothioate oligonucleotide moiety may be combined with a cationic lipid. Examples of cationic lipids include, but are not limited to, lipofectin, dotma, and dogs.

Methods of administering to the subject include intracoronary, oral, intravenous, intramuscular, intratracheal or subcutaneous administration.

In any of the methods disclosed herein the phosphorothioate oligonucleotide moiety may be administered to the subject in a pharmaceutical composition via any known mode of administration. Such means of administration are well known to those skilled in the art and include, but are not limited to, topical administration, parenteral administration, oral administration, or intraperitoneal, intravenous, intratracheal, intramuscular, or subcutaneous injection. Administration of the phosphorothioate oligonucleotide moiety may be effected continuously or intermittently. Administration may also be in combination with cationic lipids or carriers.

A pharmaceutical composition comprising a phosphorothioate oligonucleotide moiety described herein may include any of the known pharmaceutical carriers. Examples of suitable pharmaceutical carriers include any of the standard pharmaceutically accepted carriers to one of ordinary skill in the art. Examples of such pharmaceutical carriers include, but are not limited to, phosphate buffered saline solution, water, emulsions such as oil/water emulsions or a triglyceride emulsion, various types of wetting agents, tablets, coated tablets and capsules. A suitable pharmaceutically acceptable carrier may be selected taking into account the chosen mode of administration.

An effective amount of a pharmaceutical composition comprising a phosphorothioate oligonucleotide moiety is that amount which is effective to bring about the desired effect in the subject. Accordingly, an effective amount will depend on various factors known to those of ordinary skill in the art. Such factors include, but are not limited to, the size of the subject and the degree to which the disease from which the subject suffers has progressed. The effective amount will also depend on whether the phosphorothioate oligonucleotide moiety is going to be administered to the subject in a single dosage or periodically over a stretch of time.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

Material and Methods

Materials

S-dC28, S-dC14, ZK 10 (5' G-G-G-G-G-G-G-C-C-C-C-G-G-G-C-C-C-C 3') and ZK 14 (5' G-G-G-G-G-G-G-G-G-C-C-G-G-G-C-C-A-T 3') were synthesized on an Applied Biosystems (Foster City, Calif.) model 380B DNA synthesizer and purified with reverse phase high pressure liquid chromatography as previously described [16]. Platelet-derived growth factors BB, AA and AB (PDGF), basic fibroblast growth factor (bFGF), and epidermal growth factor (EGF) were purchased from Upstate Biotechnology Inc. (Lake Placid, N.Y.); CytoTox 96™ cytotoxicity assay system and CellTiter 96™ AQ proliferation assay kits were purchased from Promega Corporation (Madison, Wis.). Fetal Bovine Serum (FBS) and Medium 199 (M199) were purchased from GIBCO (Grand Island, N.Y.).

Cell Culture

Human aortic smooth muscle cells were obtained from Clonetics (San Diego, Calif.) and subcultured using smooth muscle growth medium (Clonetics) containing human epidermal growth factor (10 ng/ml), human fibroblast growth factor (2 ng/ml), dexamethasone (0.39 $\mu$g/ml), 5% FBS, gentamycin (50 $\mu$g/ml), and amphotericin-B (50 ng/ml) at 37° C. in a humidified 95% air–5% $CO_2$ atmosphere. The growth medium was changed every other day until confluence was reached. The cells used for experiments were from passages #5–10. Verification of SMC phenotype was performed via positive fluorescent staining for $\alpha$-actin (compared to a known positive control for SMC) and negative staining for Factor VIII antigen. Cell viability was 95% or greater as determined by trypan blue exclusion at the end of experiments.

SMC Proliferation Assay

Human aortic smooth muscle cells were grown to 60–70% confluence in 12 well tissue culture plates (22.6 mm diameter, Costar, Cambridge, Mass.) SMC were then washed 3 times with basal M199 and incubated with serum free medium (M199 supplemented with 0.2% bovine albumin) for 48 hours to obtain quiescent non dividing cells as previously described [17]. Thereafter, cells were incubated with equal volumes of vehicle alone, 10% FBS alone, PDGF 100 ng/ml alone, PDGF 100 ng/ml in combination with various concentration of S-dC28, or PDGF 100 ng/ml in combination with various concentration of S-dC28 for 48 hours at 37° C. in a humidified 95% air–5% $CO_2$ atmosphere. SMC were trypsinized and cell numbers were immediately determined by triplicate counts with a Coulter Counter (Model Z1, Coulter Electronics, Beds., England). The aforementioned experiments were also conducted using different dimeric forms of PDGF BB, AA and AB. The above experiments were duplicated using S-dC14 and ZK oligos instead of S-dC28. The aforementioned proliferation experiments were also performed with other SMC mitogens instead of PDGF, including bFGF, EGF, and 10% FBS. In additional experiments, SMC were treated with S-dC28 (20 $\mu$M) either 2 hours before or 2 hours after PDGF (100 ng/ml). In other experiments, SMC were treated with S-dC28 (20 $\mu$M) for 2 hours, followed by the addition of PDGF (100 ng/ml) after washing with medium three times. In another experiment, SMC were treated with the same doses of S-dC28 and PDGF which had been pre-incubated in a test tube for 2 hours. In order to examine the effects of S-dC28 on other SMC mitogens, the proliferation experiments were also performed with bFGF and EGF.

SMC Adhesion Assay

Human aortic smooth muscle cells were added to six-well tissue culture plates at a concentration of $5 \times 10^5$ cells/ml in M-199 supplemented with 0.2% BSA. Equal volumes of S-dC28 were then added to yield final concentrations ranging from 0.02–20 $\mu$M. Cells were incubated for 16 hrs and allowed to attach to the wells' surfaces. In certain experiments in which the adhesion assay used laminin-coated plates, fibronectin-coated plates or media containing 5% fetal bovine serum in M199 instead of 0.2% BSA in M199, the incubation period was 2 hours. Media containing non-adherent cells were removed, and cell numbers were immediately determined by triplicate counts with a Coulter Counter (Model Z1, Coulter Electronics, Beds, England). Adherent cells were trypsinized and counted. The results were also documented by photos taken of each group.

SMC Lactate Dehydrogenase Release

To determine whether S-dC28 reduces cell number by causing direct cytotoxicity, SMC LDH release was measured after a 48 hour incubation using the Promega CytoTox 96™ cytotoxicity assay system, a highly sensitive non-radioactive cytotoxicity assay for human target cells [18]. Briefly, SMC were seeded to 96 well tissue culture plates and incubated with serum free medium for 48 hours to obtain quiescent nondividing cells [17]. Thereafter, cells were incubated with equal volumes of vehicle alone, PDGF 100 ng/ml alone, or PDGF 100 ng/ml in combination with various concentrations of S-dC28 for 48 hours at 37° C. in humidified 95% air–5% $CO_2$ atmosphere. The experiments were conducted in quadruplicate. LDH release from SMC was measured as previously described [18] and results were expressed as a percentage of maximum release. LDH release was utilized instead of $^{51}$ chromium release for SMC cytotoxicity study because the latter is less useful in prolonged experiments (48 hours) due to high $^{51}$ chromium spontaneous release. SMC viability with the same treatment and incubation periods was also determined by trypan blue exclusion studies in the parallel experiments. Briefly, SMC were trypsinized and stained with 0.2% trypan blue for 1 minute before counting the cells in a hemocytometer.

Tetrazolium Calorimetric Proliferation Assay

A tetrazolium-based non-radioactive proliferation assay, an alternative to $^3$H-thymidine incorporation, was used to determine SMC proliferation. This assay was shown to correlate with $^3$H-thymidine incorporation for determination of the growth factor content of several samples [19]. Briefly, SMC were seeded to 96 well tissue culture plates and incubated with serum free medium for 48 hours to obtain quiescent nondividing cells [17]. Thereafter, cells were incubated with equal volumes of vehicle alone, PDGF 100 ng/ml alone, PDGF 100 ng/ml in combination with various concentrations of S-dC28 for 48 hours at 37° C. in a humidified 95% air–5% $CO_2$ atmosphere. Tetrazolium reagents were added 4 hours before reading the plates with an ELISA card reader. The experiments were conducted in quadruplicate.

SMC Migration

SMC migration activity was assayed in a modified micro Boyden chamber [20,21] using a polycarbonate filter of 8.0 $\mu$m (diameter) pore size (Costar, Cambridge, Mass.) to divide the upper and lower well chambers. Cultured human aortic SMC were trypsinized and suspended at a concentration of $5 \times 10^5$ cells per ml in M199 supplemented with 0.2% bovine albumin. A volume of one ml of cell suspension was placed in the upper chamber, and 2 ml of the same medium containing vehicle, PDGF (50 ng/ml) or PDGF in combination with varying concentrations of S-dC28 were loaded in the lower chamber of the apparatus. After 48 hours of incubation (37° C., 5% $CO_2$ in air), the cells on the upper and lower sides of the filter were trypsinized and counted using a Coulter Counter (Model Z1, Coulter Electronics, Beds., England). Migration activity was determined by the ratio of cell number of triplicate counts in the upper and lower chambers of the apparatus.

Rat Balloon Injury Studies

Male Sprague-Dawley rats (Charles River Breeding Laboratories, Wilmiton, Mass.), weighing 400–500 grams were used. Due to the stress of shipping, all rats were quarantined for at lease 5 days before use. Each animal was anesthetized with an intraperitoneal injection of 100 mg/kg ketamine (Ketalar; Parke Davis, Morris Plains, N.J.), and 5 mg/kg of xylazine (Rompum; Mobay Corporation, Shawnee, Kans.). The right carotid artery of each animal was isolated by a midline incision, suspended on ties and stripped of adventitia as previously described [22]. A 2F Fogarty catheter was introduced through the external carotid artery of each rat, advanced to the aortic arch, the balloon was inflated in the common carotid artery to produce moderate resistance to catheter movement and then gradually withdrawn to the entry point. The entire procedure was repeated three times for each animal. Immediately after balloon angioplasty, 150 $\mu$l of solution of saline, 25% pluronic gel, or 25% pluronic gel containing S-dC28 120 $\mu$M was applied to the exposed adventitial surface of the carotid artery at the site of balloon injury. The pluronic solutions were prepared as outlined by the manufacturer (BASF Wyandotte Corporation, Wyadotte, Mich.) and maintained at 4° C. Prechilled pipettes and tips were used to apply the gel solutions to the common carotid arteries. The treated area constituted about half of the blood vessel and represented the portion that lies within the neck. On contact with tissues at 37° C., the pluronic solutions gelled instantaneously generating a translucent layer that enveloped the treated region. The wounds were closed immediately after application of gel, and the rats were returned to the cages. In some experiments, a suture was put to make dividing points of treated and untreated segments. Inspection of additional animals revealed that the pluronic gel disappeared over 1–2 hours. Fourteen days after balloon injury, the animal were anesthetized with nembutal and perfused with saline. The carotid arteries were removed, fixed in 4% formalin, and processed for light microscopy in a standard manner.

Statistics

Data are presented as the mean±standard error of the mean (SD) of the independent experiments. Statistical significance was determined by one way analysis of variance (ANOVA) and Fisher's PLSD test (StatView 4.01; Brain Power, Inc., Calabasas, Calif.). For data of treated and untreated segments of carotid arteries, a paired t test (statView 4.01) was used. A p value of $<0.05$ was considered statistically significant between the means.

Results

Effects of S-dC28 on SMC Proliferation in Vitro

Figure 1B:
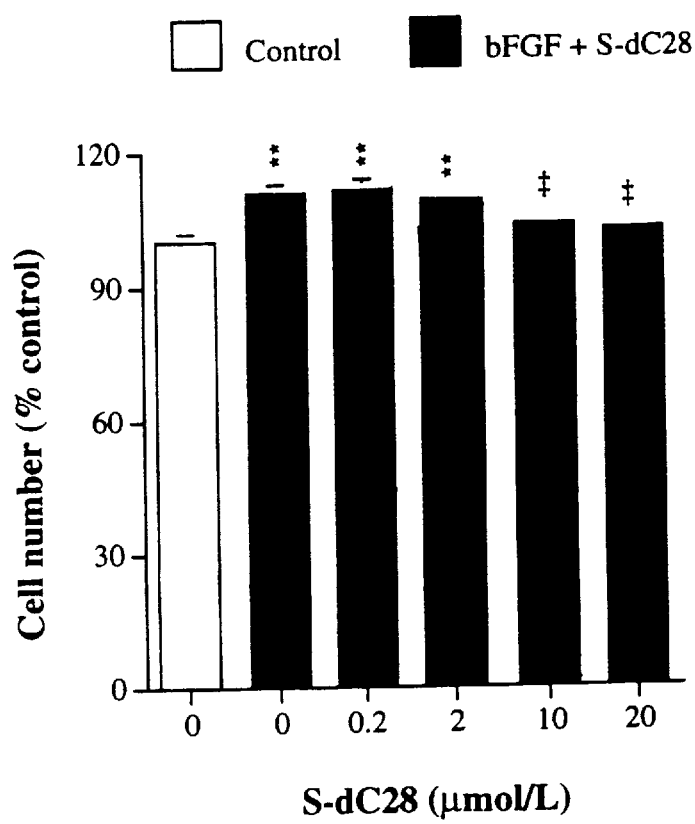
Figure 1C:
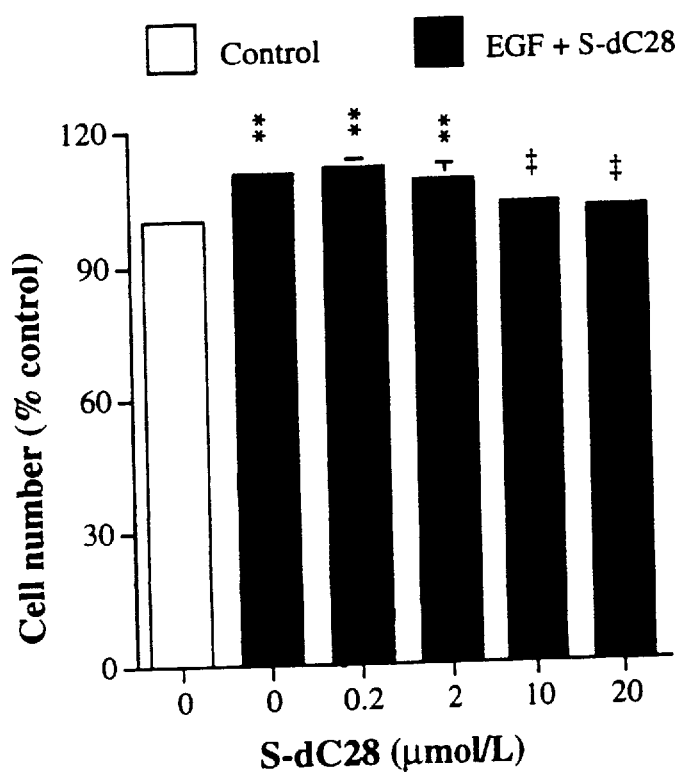
Figure 1D:
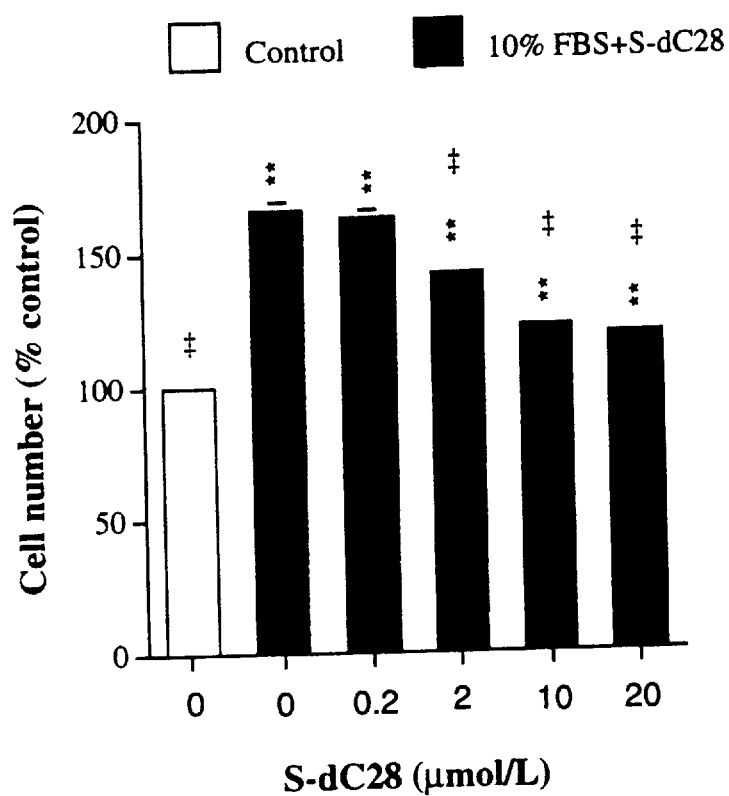

The effects of S-dC28 on SMC proliferation induced by human recombinant PDGF BB are depicted in FIG. 1A. PDGF significantly increased cell number over the value of the control group (n=7, $p<0.0001$). S-dC28 at concentrations of 10 $\mu$M (57% inhibition, $p<0.01$) and 20 $\mu$M (90% inhibition, $p<0.001$) significantly inhibited SMC proliferation induced by PDGF (n=7). S-dC28 itself did not affect SMC proliferation in serum free media. Other PS oligos such as ZK 10, ZK 14, and S-dT28, were also tested. They also inhibited SMC proliferation induced by PDGF in the same fashion as S-dC28. In order to determine whether or not S-dC28's inhibition of SMC proliferation is specific to PDGF, experiments using other SMC mitogens were conducted. Effects of S-dC28 on bFGF induced SMC proliferation are shown in FIG. 1B. bFGF (10 ng/ml) significantly increased SMC number over the control group ($p<0.0001$). SMC number after co-incubation with bFGF 10 ng/ml and S-dC28 at concentrations of 10 $\mu$M (67% inhibition, $p<0.001$) and 20 $\mu$M (76% inhibition, $p<0.001$) was significantly attenuated compared to the values of the bFGF alone group (n=5). Effects of S-dC28 on EGF induced SMC proliferation are shown in FIG. 1C. SMC number after co-incubation with 10 ng/ml of EGF was significantly increased over the value of the control group. S-dC28 at concentrations of 10 $\mu$M (63% inhibition, $p<0.01$) and 20 $\mu$M (77% inhibition, $p<0.001$) significantly inhibited SMC proliferation induced by EGF (n=4). The effects of varying concentrations of S-dC28 on SMC proliferation induced by 10% FBS (FIG. 1D) were also examined. SMC number after co-incubation with 10% FBS was significantly increased over the value of the control group. S-dC28 at concentrations of 10 $\mu$M (66% inhibition, $p<0.001$) and 20 $\mu$M (72% inhibition, $p<0.001$) significantly inhibited SMC proliferation induced by 10% FBS (n=8). To determine whether S-dC28's effects on SMC proliferation are a result of its cytotoxic effects on SMC, SMC LDH release was measured after a 48 hour incubation with various dosages of S-dC28. S-dC28 concentrations from 0.02 to 20 $\mu$M did not alter SMC LDH release (7% of maximum release in all groups) (n=6). In parallel experiments, it was also found that S-dC28 did not alter SMC viability at the end of experiments as determined by trypan blue exclusion (n=6).

The modulation of the effects of S-dC28 on PDGF-mediated SMC proliferation are presented in Table I. Addition of S-dC28 2 hours after pretreatment with PDGF reduced SMC proliferation by 60%. S-dC28 pretreatment of SMC 2 hours before the addition of PDGF inhibited SMC proliferation by 79% ($p<0.01$). However, when SMC were preincubated with S-dC28 for 2 hours and then washed three times with medium, the subsequent addition of PDGF resulted in only a 37% attenuation in SMC proliferation. S-dC28 and PDGF preincubated in a test tube for 2 hours prior to addition to SMC reduced SMC proliferation by 63%.

In order to determine whether S-dC28's inhibition of SMC proliferation is specific to PDGF, we also conducted the experiments using other SMC mitogens. The effects of S-dC28 on bFGF-induced and EGF-induced SMC proliferation are shown in Table II. bFGF(10 ng/ml) significantly increased SMC number. SMC number after co-incubation with bFGF(10 ng/ml) and S-dC28 at concentrations of 10 $\mu$M (67% inhibition, $p<0.001$) and 20 $\mu$M (76% inhibition, $p<0.001$) was significantly attenuated compared to the values of the bFGF alone group (n=5). SMC number after co-incubation with 10 ng/ml of EGF was significantly increased. S-dC28 at concentrations of 10 $\mu$M (63% inhibition, $p<0.01$) and 20 $\mu$M (77% inhibition, $p<0.001$) significantly inhibited SMC proliferation induced by EGF (n=4). In order to test whether PS oligos other than S-dC28 have similar effects on SMC proliferation, the effect of S-dT28 on SMC proliferation induced by PDGF was studied. Similar inhibition of SMC proliferation was demonstrated (data not shown).

Effects of S-dC28 On The Tetrazolium-Based Proliferation Assay

Figure 2:
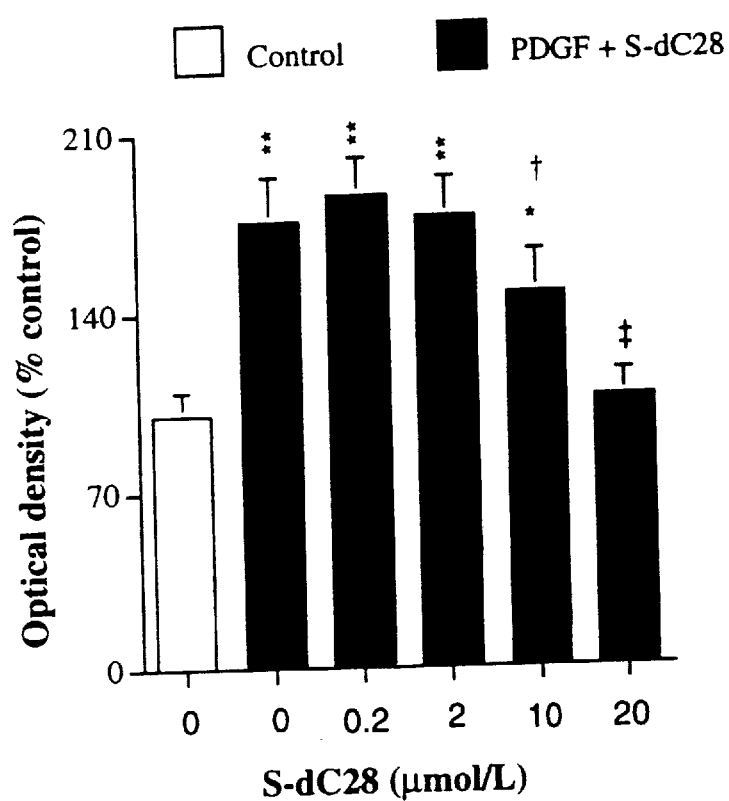
FIG. 2: Effects of S-dC28 on PDGF induced human aortic SMC proliferation measured by the tetrazolium-based proliferation assay. Growth-arrested human aortic SMC were incubated with vehicle alone, PDGF (100 ng/ml) alone, or PDGF (100 ng/ml) in combination with various doses of S-dC28 for 44 hours at 37° C. in a humidified 5% $CO_2$ atmosphere. Tetrazolium-dye solution were added and SMC were incubated for an additional 4 hours. Optical density was determined by an ELISA card reader. Values are mean ± SD (n=6) . (*$p<0.05$, **$p<0.01$ relative to control SMC cultured in media alone; †$p<0.05$, ‡$p<0.0l$ compared to the PDGF alone group).

The effects of S-dC28 on the tetrazolium-based proliferation assay are depicted in FIG. 2. This proliferation assay is a non-radioactive alternative to $^3$H-thymidine incorporation for the determination of the viable cell number. PDGF significantly increased SMC proliferation in the tetrazolium-based proliferation assay over the value of the control group (n=7, $p<0.001$). S-dC28 at concentrations of 20 $\mu$M (99% inhibition, $p<0.01$) and 10 $\mu$M (52% inhibition, $p<0.001$)

significantly inhibited SMC proliferation induced by PDGF (n=5). S-dC28 alone did not affect SMC proliferation in serum free media. These results which reflect DNA synthesis in SMC, were well correlated to the direct cell counts.

Effect of S-dC28 on in Vitro SMC Migration

SMC migration studies using a modified micro-Boyden chamber are shown in FIG. 3. PDGF (50 ng/ml) was used as positive control. PDGF induced SMC migration from the upper chamber to the lower chamber (268±42%) significantly greater than the value of SMC migration in the control group. S-dC28 at concentrations of 2 $\mu$M (p<0.011), 10 $\mu$M (p<0.003) and 20 $\mu$M (p<0.002) significantly inhibited SMC migration induced by PDGF in a dose-dependent fashion (n=4). The effects of other PS oligos such as S-dT28 and ZK 10 on SMC migration were also examined. Similar results to those obtained with S-dC28 were observed with these PS oligonucleotides as well.

Figure 4A:
FIGS. 4A–4C: Effects of S-dC28 on neointimal formation in rat carotid arteries subjected to balloon angioplasty. Representative cross-sections are shown from the carotid artery of an untreated rat (FIG. 4A), a rat treated with pluronic gel alone (FIG. 4B), and a rat treated with pluronic gel containing S-dC28 (FIG. 4C) (Nikon, magnification ×80). The tissue were H & E stained for microscopy in a standard manner.
Figure 4B:
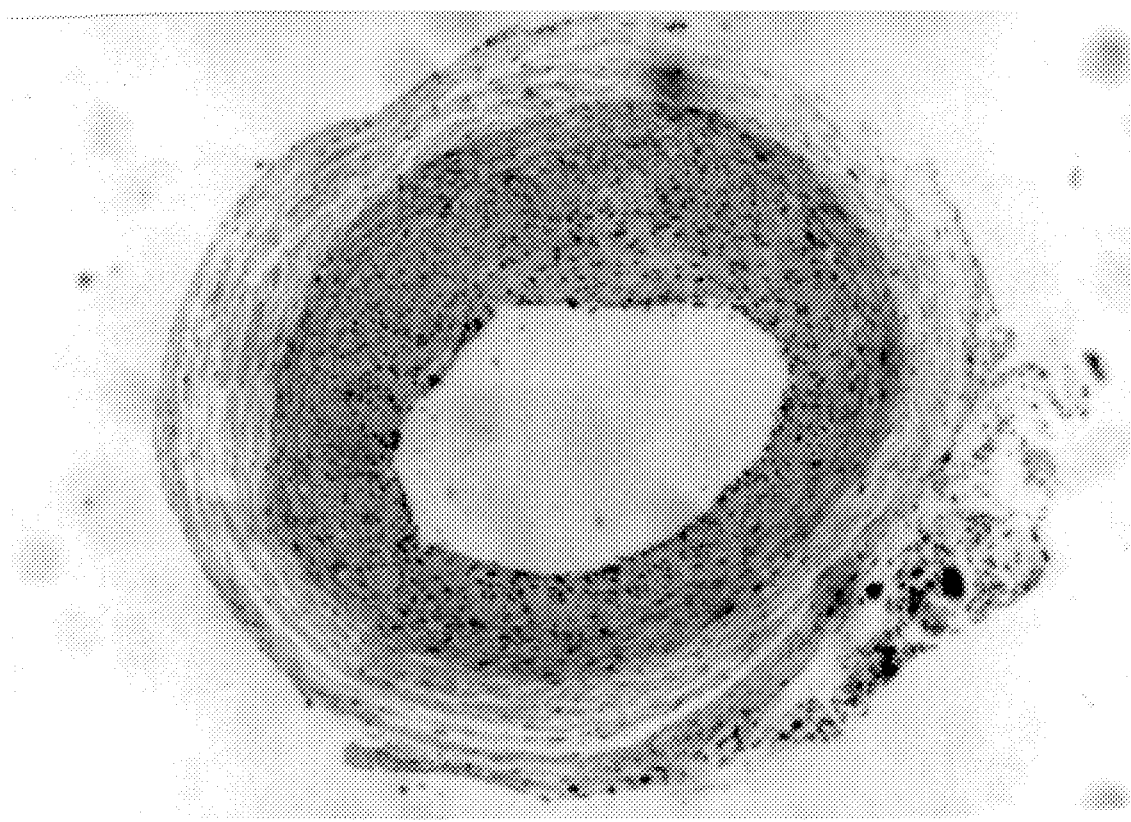
Figure 4C:
Figure 5A:
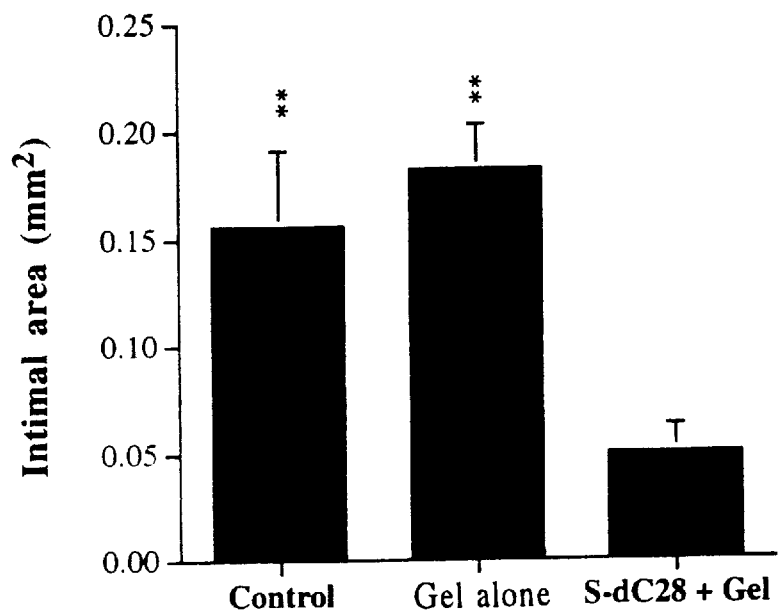
FIGS. 5A and 5B: Effects of S-dC28 on rat common carotid artery neointimal cross section area (FIG. 5A) as well as intima/media ratio (FIG. 5B). Rat carotid arteries after balloon injury were treated with saline (control group, n=4), pluronic gel alone (gel group, n=7), and pluronic gel containing S-dC28 (S-dC28 +gel group, n=9) for 14 days. All the measurements were done in a blinded fashion. Values are mean ± SD. (**$p<0.01$ relative to the S-dC28+gel group).
Figure 5B:
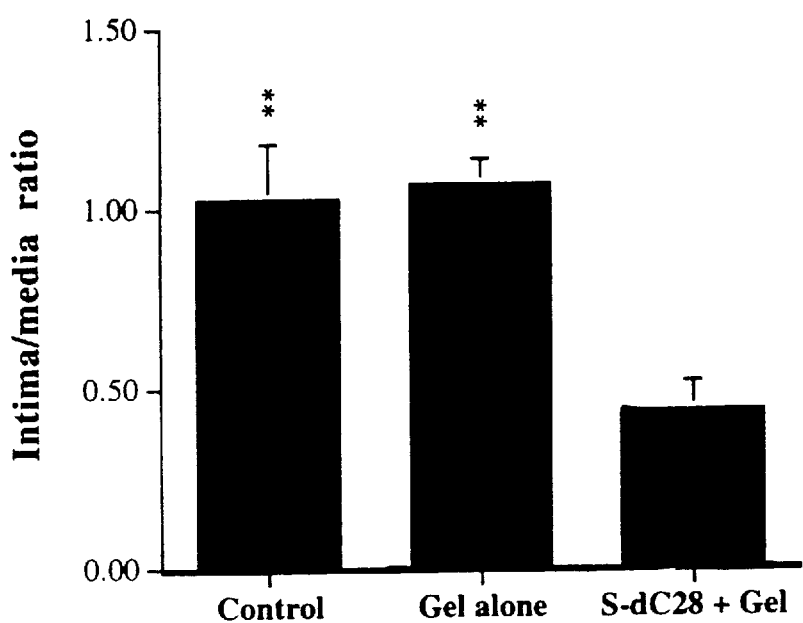

Effects of S-dC28 on Neointima Formation of Rat Carotid Arteries After Balloon Angioplasty Injury To examine whether S-dC28 also suppresses SMC proliferation and migration in vivo, the rat right carotid artery balloon angioplasty model was utilized. This model denudes endothelium and induces a highly reproducible neointimal proliferation and migration of SMC over the entire length of the injured blood vessel [23,24]. The effects of S-dC28 on intimal SMC accumulation were determined 2 weeks after angioplasty in 20 rats which were treated with pluronic gel containing S-dC28 (n=9), pluronic gel alone (n=7), or saline (n=4). Morphological examination revealed that minimal neointimal accumulation developed in the S-dC28 treated group, whereas extensive neointimal accumulation was observed in the pluronic gel alone and saline groups (FIG. 4). The measurements of arterial segments demonstrated that S-dC28 (n=9) suppressed the neointimal SMC accumulation (cross section area) compared the values in the saline group (n=4, p<0.004) and the pluronic gel group (n=7, p<0.0001; FIG. 5A). Furthermore, the intima/media area ratio was significantly reduced by S-dC28 treatment over the values of the saline group (n=4, p,0.0006) and the pluronic gel group (n=7, p<0.0001), indicating minimal effects on medial SMC growth (FIG. 5B).

Figure 6:
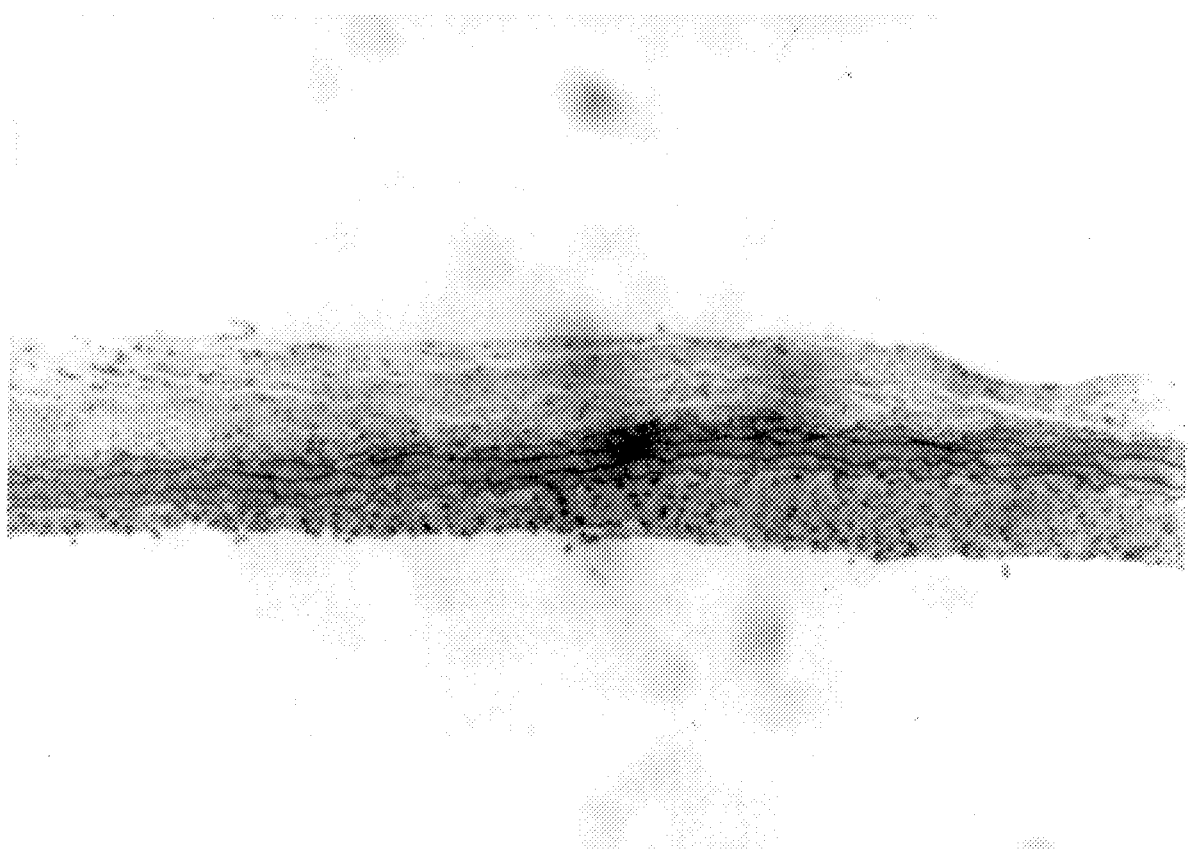
FIG. 6: Spatial distribution of the antiproliferative effects of S-dC28. The longitudinal section of the transitional area between the treated and untreated zones (Nikon, magnification ×80) is depicted on the left; typical cross sections (Nikon, magnification ×80) from treated and untreated segments of the right carotid artery of a rat are shown on the right. The shaded area represents the extent of application of pluronic gel.
Figure 7:
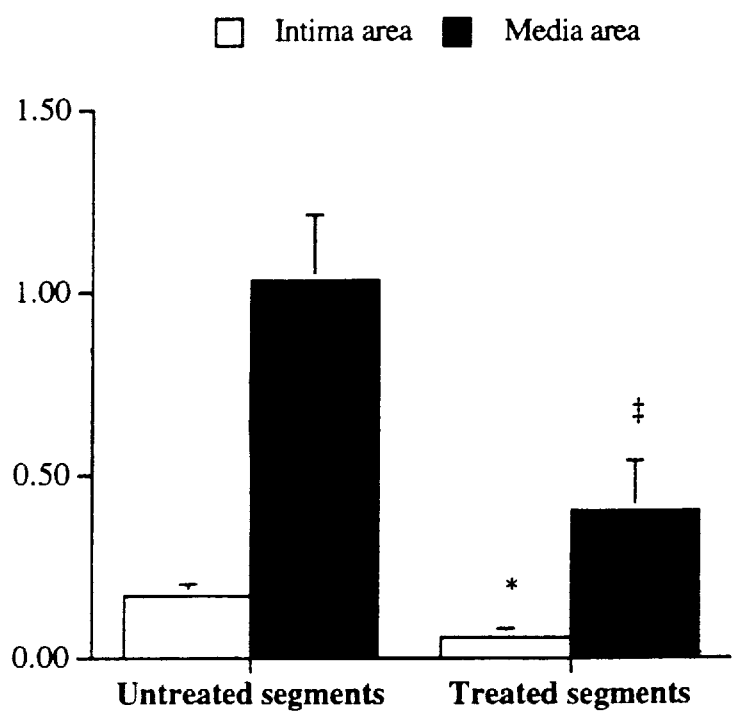
FIG. 7: Effects of S-dC28 on rat common carotid artery neointimal cross-sectional area as well as the intima/media ratio in treated and untreated segments. Rat carotid arteries after balloon injury were treated with pluronic gel plus S-dC28 (S-dC28 +gel group, n=9) for 14 days. Treated segments represented the neck portion of common cartoid arteries while untreated segments represented the chest portion of the same arteries which had no S-dC28 treatment. All the measurements were done in a blinded fashion. Values are mean±SD. (**$p<0.01$ relative to the S-dC28 +gel group).

Rat carotid arteries were also examined to evaluate the longitudinal extent of suppression of neointimal SMC accumulation. FIG. 6 shows a representative transitional region of a treated zone (in the neck) and an untreated zone (in the chest) of the same blood vessel which was demarcated with a silk tie. Similar patterns of suppression of SMC accumulation by S-dC28 were seen in other rats. The measurements of the treated arterial segments and the untreated segments documented that S-dC28 significantly suppressed the neointimal SMC accumulation in the treated zones (neointima area p<0.017; neointima/media area ratio p<0.017) compared to the values in the untreated zones (n=5, FIG. 7).

Effects of S-dC28 on SMC Adhesion

Figure 8A:
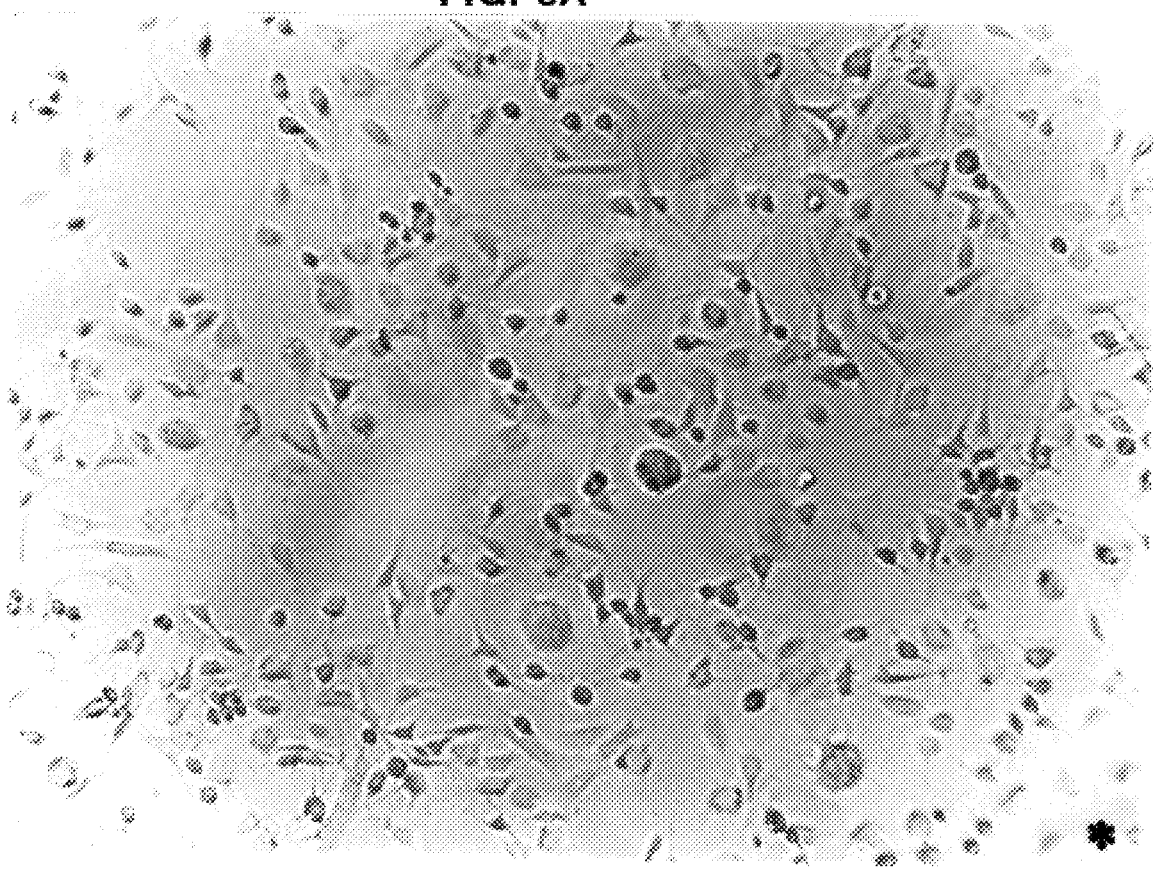
FIGS. 8A–8D: Morphological Effects of S-dC28 on Human Aortic SMC Adhesion. Growth-arrested human aortic SMC were incubated with vehicle alone or various doses of S-dC28 in medium 199 containing 0.2% bovine albumin for 16 hours at 37° C. in a humidified 5% $CO_2$ atmosphere. Representative pictures are shown from SMC incubated with 2% bovine albumin (Nikon, magnification ×100).
Figure 8B:
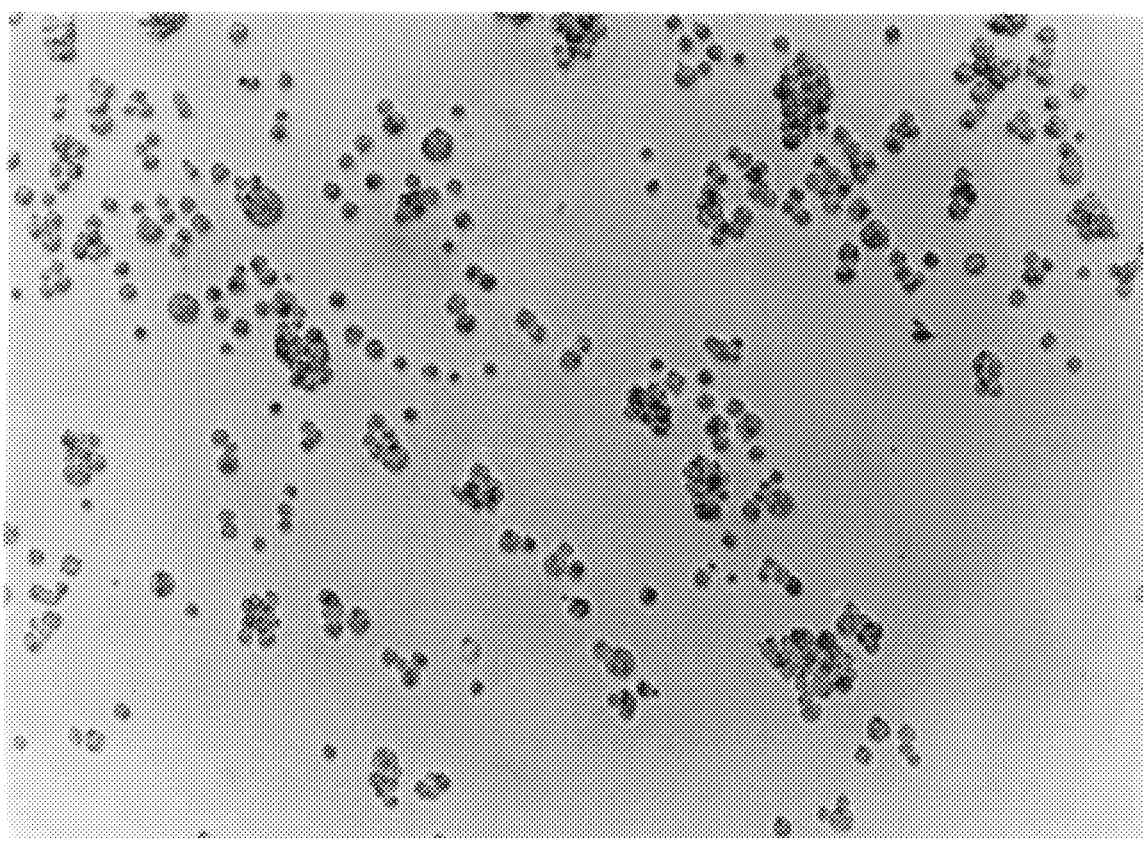
Figure 8C:
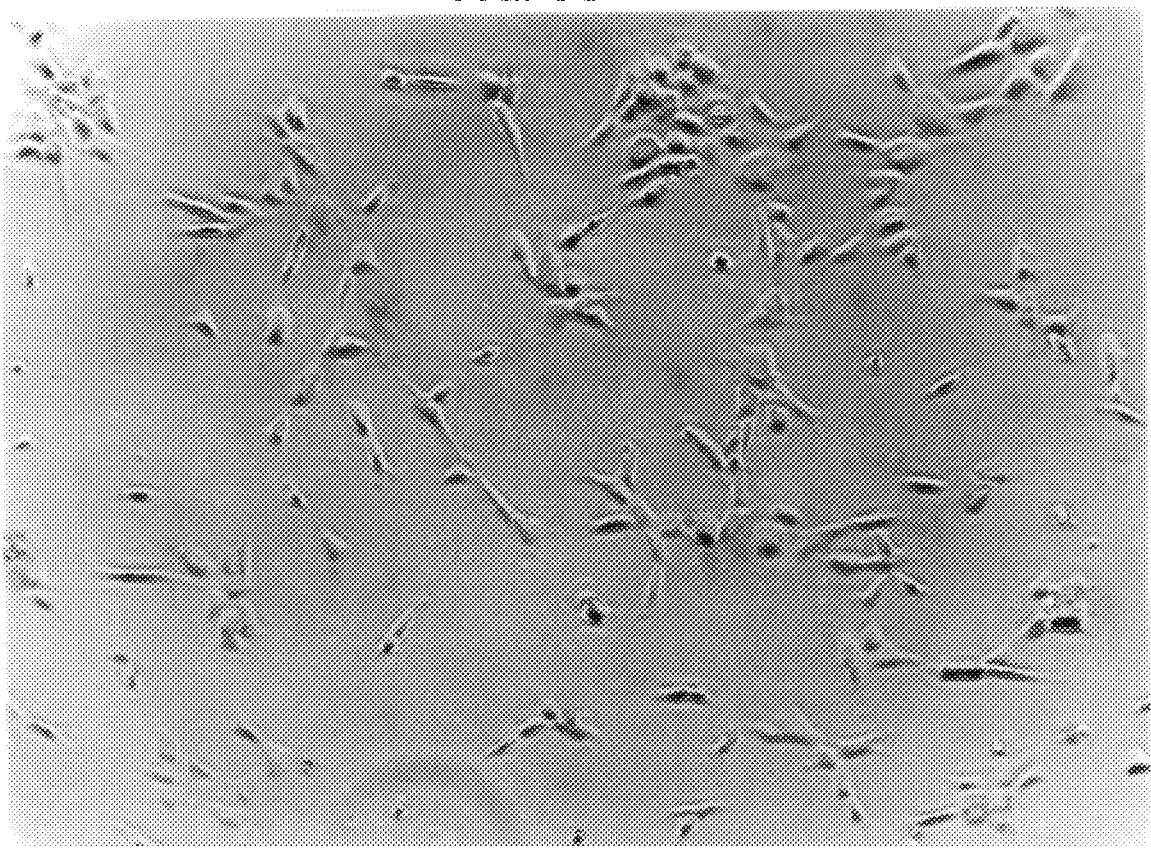
Figure 8D:
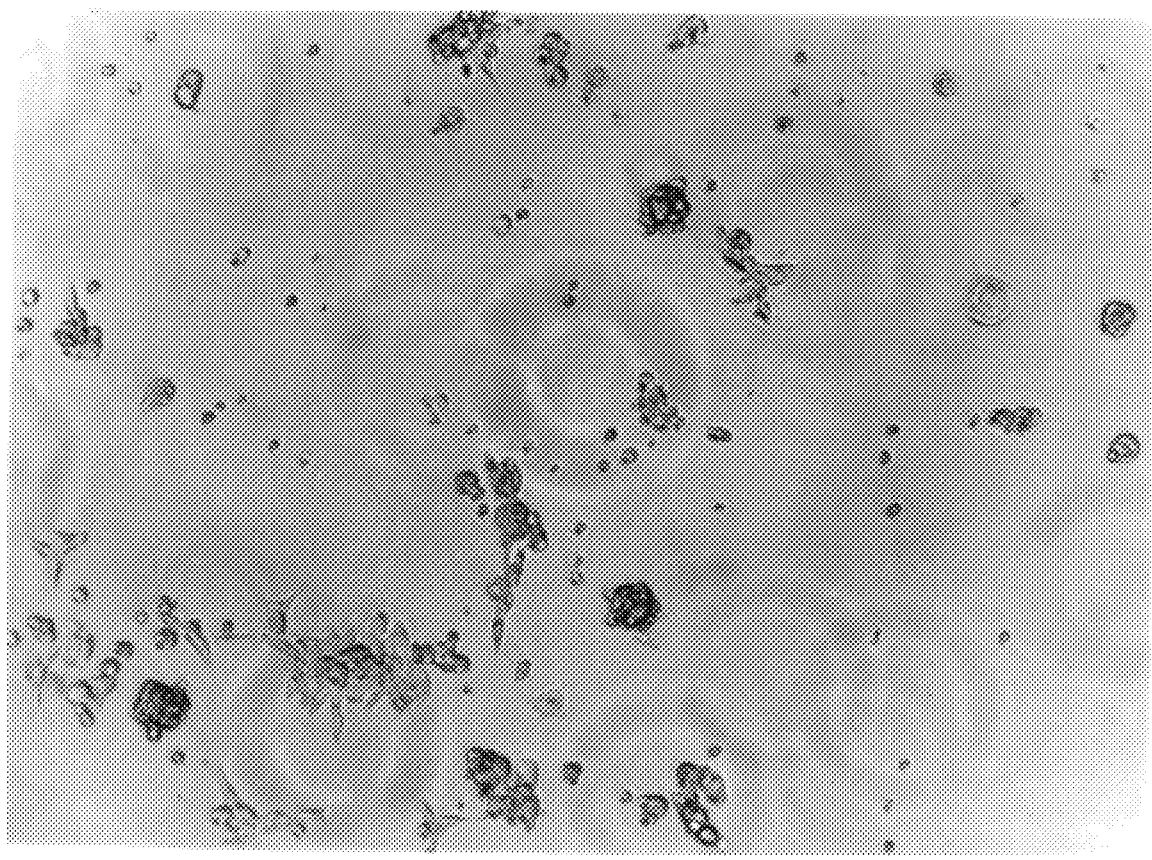
Figure 9:
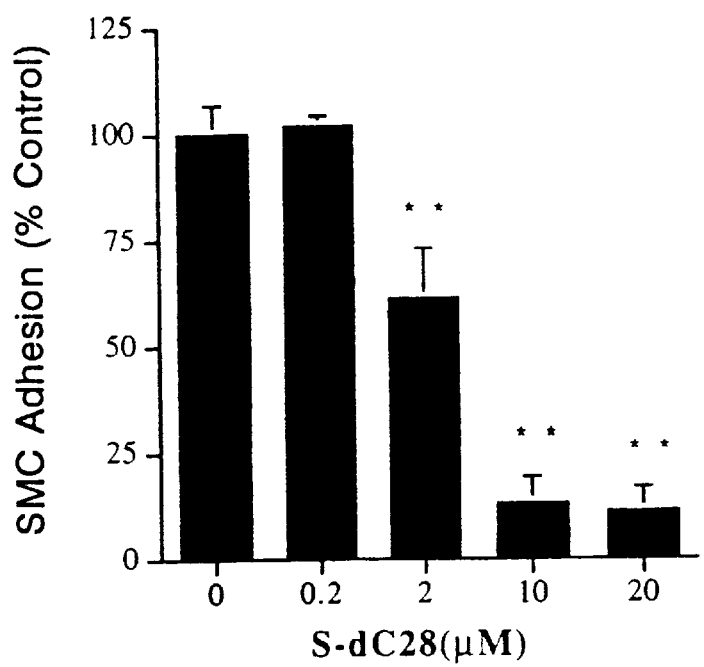
FIG. 9. Quantitative Effects of S-dC28 on Human Aortic SMC Adhesion. Growth-arrested human aortic SMC were incubated with vehicle alone or various doses of S-dC28 in medium 199 containing 0.2% bovine albumin for 16 hours at 37° C. in a humidified 5% $CO_2$ atmosphere. SMC were then trypsinized and cell numbers immediately determined by triplicate counts with a Coulter Counter. Values are mean±SD (n=6) . (** $p<0.01$ relative to control SMC cultured in media alone).

The effects of increasing doses of S-dC28 on human aortic SMC adhesion to plastic plates was studied. SMC adhesion was monitored at different time points. FIGS. 8A–8D are representative pictures at 6 hours and 16 hours. When the incubation time was 6 hours, S-dC28 at a concentration of 20 $\mu$M completely inhibited cell adhesion (FIG. 8B), while the majority of SMC adhered in the control group (FIG. 8A). When the incubation time was extended to 16 hours, only a small portion of the SMC adhered in the S-dC28 20 $\mu$M treated group (FIG. 8D), while the majority of SMC adhered in the control group (FIG. 8C). SMC in the control group had spread out and attained a typical SMC morphology. In contrast, SMC in the S-dC28 treated group were not spread out and did not develop a typical SMC morphology. In order to quantitate SMC adhesion, SMC number was counted by Coulter Counter (FIG. 9). S-dC28 at concentrations of 2 $\mu$M (39% inhibition, p<0.001) , 10 $\mu$M (86% inhibition, p<0.001), and 20 $\mu$M (88% inhibition, p<0.001) dose-despondently inhibited SMC adhesion (n=5) compared to the value of the control group.

Modulation of S-dC28's Inhibitory Effects on SMC Adhesion by Fibronectin, Laminin and FBS In order to determine whether fibronectin and laminin alter S-dC28's inhibition of SMC adhesion, SMC were pre-incubated with varying doses of S-dC28 for 30 minutes and then transferred to human fibronectin- or laminin-coated plates. SMC adhesion dramatically improved in all groups (Table III). At 2 hours, SMC adhesion in fibronectin-coated plates demonstrated much less pronounced inhibition with S-dC28 at concentrations of 10 $\mu$M (26% inhibition, p<0.0l) and 20 $\mu$M (25 % inhibition, p<0.01 (n=4)). When laminin-coated plates were used, the inhibition of SMC adhesion by S-dC28 was completely reversed (n=5) (Table III). Replacement of serum-free media with 5% fetal bovine serum media for SMC cultured on non-coated plates also greatly attenuated inhibition of adhesion by S-dC28 at doses of 10 $\mu$M (13% inhibition, p<0.01) and 20 $\mu$M (9% inhibition, p<0.01) (n=5)(Table III).

Discussion

Phosphorothioate oligodeoxynucleotides (PS oligos) are antisense (sequence-specific) inhibitors of vascular smooth muscle cell (SMC) proliferation when targeted against different genes. Recently an aptameric G-quartet inhibitory effect of PS oligos has been demonstrated. To determine whether PS oligos manifest non-G-quartet, non-sequence specific effects on human aortic SMC, the effects of S-dC28, a 28-mer phosphorothioate cytidine homopolymer, on SMC proliferation induced by several SMC mitogens were examined. SMC proliferation was determined by a tetrazolium-based proliferation assay, which correlates to DNA synthesis, and by Coulter Counter direct determination of cell number. S-dC28 inhibited SMC proliferation induced by the mitogens platelet-derived growth factor (PDGF), basic fibroblast growth factor (bFGF), epidermal growth factor (EGF), and 10% FBS without cytotoxicity. S-dC28 abrogated PDGF-induced in vitro migration in a modified micro-Boyden chamber. Furthermore, S-dC28 manifested in vivo antiproliferative effects in the rat carotid balloon injury model. S-dC28 suppressed neointimal cross-sectional area by 73% and the intima/media area ratio by 59%. Therefore, PS oligos exert potent non-G-quartet, non-sequence specific effects on in vitro SMC proliferation and migration as well as in vivo neointimal formation.

The sequence-independent effects of phosphorothioate oligodeoxynucleotides (PS oligos) on SMC adhesion by using S-dC28, a 28 mer phosphorothioate cytidine homopolymer which lacks any guanosines, were also studied. Human aortic SMC were incubated with vehicle or various doses of S-dC28, and the number of SMC adhered to non-coated plates was determined using a Coulter Counter, S-dC28 at concentrations of 2 $\mu$M (39% inhibition, p<0.001), 10 $\mu$M (86% inhibition, p<0.001), and 20 $\mu$M (88% inhibition, p<0.001) significantly inhibited SMC adhesion. SMC adhesion dramatically improved with S-dC28 at 10 $\mu$M (26% inhibition, p<0.01), and 20 $\mu$M (25% inhibition, p<0.01) in fibronectin-coated plates. When laminin-coated plates were used, the inhibition of SMC adhesion by S-dC28 was completely reversed. Replacement of serum-free media with 5% fetal bovine serum media for SMC cultured on non-coated plates also greatly attenuated inhibition of adhesion by S-dC28 at doses of 10 μM (13% inhibition, p<0.01), and 20 μM (9% inhibition, p<0.01). Therefore, PS oligos inhibit human SMC adhesion via a non-G-quartet, non-sequence specific mechanism, and that this inhibition can be diminished by fibronectin- or laminin-coating of culture plates or by the presence of serum in the culture media.

In this study, it was demonstrated that PS oligos manifest non-G-quartet, non-sequence specific antiproliferative effects on SMC in vitro and in vivo. In particular, S-dC28 inhibited human aortic SMC proliferation in vitro as determined by the SMC cell number induced by the mitogens PDGF, bFGF, EGF, and 10% FBS. In addition, S-dC28 inhibited PDGF-induction of human aortic SMC proliferation measured by a non-radioactive proliferation assay which correlates with DNA synthesis [19]. S-dC28 did not reduce cell number by causing direct cell cytotoxicity as evinced by the LDH release assay and trypan blue exclusion experiments. Moreover, S-dC28 abrogated PDGF-induced in vitro SMC migration in a modified micro-Boyden chamber. Furthermore, S-dC28 manifested striking in vivo antiproliferative effects in the rat carotid balloon injury model. S-dC28 potently suppressed neointimal SMC cross-sectional area by 73% and the intima/media area ration by 59%. S-dC28 reduced not only the cross-sectional area but longitudinally suppressed neointimal SMC accumulation. Of note, the PS oligos used in this study appeared to be well tolerated by the rats; none of the PS-oligo treated rats developed side-effects or died prior to sacrifice. This sequence-independent inhibition manifested by PS oligos that we observed on SMC proliferation and migration in vitro and neointimal hyperplasia in vivo after balloon injury is most likely a reflection of PS oligo inhibition of the activity of SMC growth factors through PS oligo binding to growth factors and to cellular and. extracellular proteins at multiple sites.

S-dC28 inhibited in vitro SMC proliferation by 10% FBS as well as by PDGF, bFGF and EGF. Most of the large effect observed with 10% FBS may have represented inhibition by S-dC28 of PDGF present in FBS. PDGF is the major mitogen present in serum that stimulates SMC DNA synthesis and cell growth [50, 51]. Moreover, S-dC28 also inhibited PDGF-induced SMC migration in vitro in a modified micro-Boyden chamber.

The sequence-independent inhibition manifested by PS oligos that was observed on SMC proliferation and migration in vitro and neointimal hyperplasia in vivo after balloon injury is most likely a reflection of PS oligo binding avidly to cellular proteins. It was demonstrated that S-dC28 inhibits in vitro SMC proliferation induced by a variety of SMC mitogens including PDGF, bFGF, EGF, and 10% FBS. Moreover, S-dC28 inhibited PDGF induction of SMC migration in vitro in a modified micro-Boyden chamber. PS oligos have been demonstrated to bind directly to heparin-binding growth factors such as bFGF (basic fibroblast growth factor), aFGF (acidic fibroblast growth factor), vascular endothelial cell growth factor, and fibroblast growth factor-4 [15]. Thus, PS oligo binding to a variety of heparin-binding growth factors is similar to that of other polyanions such as suramin and pentosan polysulfate [15]. Periadventitially administered sulfated β-cyclodextrin polymer, which tightly binds heparin-binding growth factors, induces sustained inhibition of intimal thickening in vivo. [60] By a gel mobility shift assay and radioreceptor assay, it has been demonstrated that S-dC28 binds directly to PDGF and bFGF but not to EGF [15]; this binding occurs with chain length dependency. S-dC28 was found to inhibit bFGF-induced DNA synthesis in NIH 3T3 cells [15]. Although 18-mer PS oligos inhibit in vitro bFGF binding for both the high and low affinity classed of bFGF receptor, the inhibition is sequence-selective only for the high affinity receptors [15]. Furthermore, PS oligos release bFGF bound to low affinity receptors in the extracellular matrix [15].

Direct binding of S-dC28 to PDGF may account for some of the reduced activity of PDGF to stimulate SMC proliferation when it is preincubated with S-dC28 for 2 hours prior to treatment of the cells (Table I). S-dC28 may also inhibit the growth promoting activity of SMC mitogens by binding to their receptors on cells. In this study, the partial reversal by washing of the inhibition of PDGF-induced SMC proliferation by S-dC28 that had been preincubated with the cells is consistent with an inhibitory effect of S-dC28 on cell surface (Table I).

Previous studies have shown that S-dC28 is taken up by human cells in vitro both by fluid phase pinocytosis and adsorptive endocytosis [52]. Internalized S-dC28 may bind to cellular proteins in both the cytoplasm and nucleus [52]. Indeed, in this study, maximal inhibition of SMC proliferation was obtained by preincubation of SMC with S-dC28 for 2 hours prior to the addition of PDGF. Therefore, in addition to its binding to PDGF extracellularly or its inactivation of PDGF on the cell surface, it is possible that S-dC28 inactivates signal transduction mechanisms within the cell cytoplasm or nucleus.

Inhibition of the actions of both PDGF and bFGF by direct binding to PS oligos could explain our findings of the in vivo antiproliferative effects of the PS oligos. Indeed, PDGF is a potent SMC mitogen which has been implicated in SMC migration [20,25]. An intravenous infusion of PDGF-BB for 7 days after rat balloon injury resulted in a 15-fold increase in the neointimal lesion area, principally increasing SMC migration [20]. bFGF is a SMC mitogen [26] and PDGF-induction of bFGF has been postulated to play an important role in SMC migration [27]. However, it is interesting to note that although S-dC28 binds directly to PDGF and bFGF but not to EGF, it inhibits SMC mitogenesis induced by all three mitogens. Therefore, despite the disparate PS oligo binding properties, PS oligo inhibition of all three mitogens suggests a common pathway of inhibition, possibly at the level of cell surface receptors or via inhibition of an intracellular signal transduction pathway.

The potent in vivo antiproliferative effects of S-dC28 may reflect the importance of bFGF in early vascular lesion formation after balloon injury in the rat carotid model. Balloon-injury induced release of endogenous bFGF stored in the extracellular matrix has been implicated in the early progress of vascular lesions in the rat carotid artery after balloon injury [26]. Systemically administered bFGF increased rat vascular SMC proliferation in arteries denuded with a balloon catheter by 54.8% compared to 11.5% in controls [26]. Administration of a neutralizing antibody directed against bFGF inhibits the first wave of intimal proliferation but not the final extent of SMC growth [28]. Therefore, S-dC28's pleiotropic inhibitory effects and its ability to bind to not only bFGF but also PDGF, in addition to its ability to inhibit a variety of mitogens by a common pathway, render it to be a very effective and potent antiproliferative agent.

PS oligos have also been demonstrated to modulate in vitro cellular adhesion through additional non-sequence specific effects. PS oligos have been shown to bind to various elements of the extracellular matrix of NIH 3T3 cells such as laminin and fibronectin. PS oligos inhibit the binding of laminin to bovine brain sulfatide. Moreover, PS oligos, in a non-sequence specific manner, inhibit the binding of fluoresceinated fibronectin to its cell surface receptor in phorbol-12, 13-myristate acetate-treated Jurkat cells. The interaction of PS oligos with extracellular matrix proteins of SMC may modulate SMC adhesion and effect a SMC phenotypic change from the synthetic state to the contractile state.

Another nonspecific effect of the PS oligos which may explain their SMC antiproliferative potential is their ability to induce the formation of gamma interferon [5]. Gamma interferon is a potent inhibitor of in vitro vascular SMC proliferation and the expression of the differentiation-specific α-smooth muscle actin antigen in tissue culture [29,30]. In addition, it inhibits in vivo formation of arterial proliferative lesions after rat carotid balloon injury [31]. Moreover, gamma interferon is also a pleiotropic inhibitor of SMC migration induced by PDGF and other promigratory cytokines [32].

S-dC28 manifested extremely potent in vivo antiproliferative effects in the rat carotid balloon injury studies, effecting a 73% decrease in neointimal cross-sectional area and a 59% decrease in the intima/media area ratio when delivered in pluronic gel without vector. These results compare favorably with respect to the degree of inhibition exerted by S-dC28 when considered against other oligonucleotides previously studied. Antisense oligonucleotides targeted against c-myb have effected a 95% reduction in the intima/media ratio in one study [13], but had no significant inhibition in a more recent study [5]. Oligonucleotides targeted against cyclin proto-oncogenes studied by two groups have revealed a proportionate reduction in the intima/media ratio of 95%, 60% and 47%, respectively [33–35]. An anti-c-myc oligonucleotide resulted in a 65% decrease in the intima/media ratio [7], while PS oligos directed against proliferating-cell nuclear antigen resulted in an 80% decrease [36]. The results are similar to the 58% reduction in the intima/media ratio effected by an oligonucleotide directed against c-myc in the porcine model of balloon injury [8].

In this study, it was also demonstrated that the PS oligo (S-dC28, a 28-mer phosphorothioate cytidine homopolymer lacking quanosines, significantly inhibits human aortic SMC adhesion in vitro in a non-G-quartet, non-sequence specific manner. The ECM proteins laminin and fibronectin both decrease the inhibition of SMC adhesion effected by S-dC28. Furthermore, S-dC28-mediated inhibition of human aortic SMC adhesion was significantly diminished by the presence of serum in the culture media. It should also be noted that whereas laminin-coating of plates completely reversed S-dC28-mediated inhibition of SMC adhesion, fibronectin-coating of plates resulted in a 75% decrease in S-dC28-mediated inhibition of SMC adhesion. This difference may reflect the differential binding patterns of PS oligos to laminin versus fibronectin. PS oligos bind to the ECM of NIH 3T3 cells as well as to ECM laminin and fibronectin [53]. PS oligo non-sequence specific binding to laminin occurs on the A subunit of laminin, occurring at or near the heparin-binding site, as evidenced by competition of this binding by discrete synthetic heparin mimetics [53]. Furthermore, PS oligos non-sequence specifically inhibit the binding of laminin to its ligand, bovine brain galactosylceramide sulfate (sulfatide), thereby preventing laminin from binding to sulfatide on which cells superficially spread [53].

In contrast, the binding of PS oligos to fibronectin appears to be more complicated than their binding to laminin [53]. Each of fibronectin's two polypeptide chain possess a heparin binding site [54]. Moreover, PS oligos non-sequence specifically inhibit fibronectin's binding to the α5β1 integrin receptor present on phorbol-12, 13-myristat acetate Jurkat cells, which may induce NF-KB activity, thereby further reducing the ability of cells to adhere and spread [53]. Although the binding of PS oligos to fibronectin is significantly weaker than their binding to laminin, it is also inhibited by synthetic heparin analogs [54, 53]. The binding of PS oligos to laminin, fibronectin, and other proteins such as bFGF is independent of P-chirality [55].

Another mechanism which should be considered in the anti-adhesive properties of the PS oligos involves protein kinase C. Protein kinase C is a serine/threonine kinase which plays an integral role in several cellular processes such as proliferation and differentiation [56]. PS oligos bind in a non-sequence specific manner to several protein kinase C isoforms (β1, α, δ, ε) [57]. Antisense oligonucleotides have been shown to inhibit protein kinase C-α expression in human A549 lung carcinoma cells, thereby inhibiting the induction of the cell adhesion molecule ICAM-1 mRNA by phobol esters [56].

It was also demonstrated that the presence of serum in the culture media obviates S-dC28-mediated inhibition of human aortic SMC adhesion. This observation is most likely the consequence of S-dC28 binding in a non-sequence specific fashion to several heparin binding proteins present in serum, particularly PDGF and bFGF [15]. PS oligos can inhibit the binding of human $I^{125}$-labeled bFGF to low and high affinity cell surface receptors on both NIH 3T3 and DU-145 cells [15]. Furthermore, PS oligos such as S-dC28, similar to heparin, are capable of releasing bFGF bound to low affinity receptors in the subendothelial ECM [15].

PS oligos are polyanions which share many properties including binding to heparin-binding proteins with other polyanions such as pentosan polysulfate and the drug suramin [15]. In this regard, it is significant that suramin, a bis-polysulfonated naphthylurea hexaanion, inhibits several lysosomal enzymes such as iduronate sulfatase, β-glucuronidase and hyaluronidase which are involved in glycosaminoglycan metabolism [58]. In particular, suramin inhibits heparanase, an endo-β-D-glucuronidase which degrades ECM heparan sulfates and effects degradation of the subendothelial ECM [59].

Interestingly, S-dC28 and suramin differ in their pattern of inhibition of protein kinase C [57]. Although both agents inhibit the phosphatidylserine and $Ca^{2+}$-dependent phosphorylation of an epidermal growth factor receptor octapeptide substrate, suramin's inhibition is marked by competitive/noncompetitive inhibition for ATP but noncompetition for substrate [57]. In contrast, S-dC28 inhibition is competitive for substrate and not competitive for ATP [57].

In summary, it was demonstrated that PS oligos exert non-G-quartet, non-sequence specific inhibition of in vitro SMC proliferation induced by several mitogens, in vitro SMC migration, and in vivo neointimal hyperplasia after balloon injury in the rat carotid artery model. The sequence-independent inhibition is most likely the result of avid binding of PS oligos to a variety of cellular as well as extracellular proteins, particularly the heparin-binding proteins. Therefore, PS oligos may exert potent non-G-quartet, non-sequence specific as well as G-quartet or aptameric inhibitory effects on in vitro and in vivo SMC proliferation. Both the sequence-independent and sequence-dependent properties of the PS oligos need to be considered in the design of optimal PS oligos for the prevention of angioplasty restenosis.

It was also demonstrated that the PS oligo S-dC28 inhibits human aortic SMC adhesion in vitro owing to a non-G-quartet, non-sequence specific mechanism. This inhibition can be partially reversed by fibronectin and completely reversed by laminin. In addition, the presence of serum in the culture media also diminishes the S-dC28-mediated inhibition of SMC adhesion. Taken together, these results suggest that PS oligos bind directly in a non-sequence specific manner to several critical proteins in the ECM such as laminin, fibronectin, heparan sulfate proteoglycans and bFGF, thereby inhibiting SMC adhesion. This property of the PS oligos may have ramifications for the treatment of disease processes involving SMC adhesion and motility including atherosclerosis and angioplasty restenosis.

TABLE I

Modulation of the Antiproliferative Effects of
S-dC28 on PDGF-Induced SMC Proliferation

| Group | Time of Addition (hours) | | Percentage Inhibition of SMC Proliferation |
|---|---|---|---|
| | PDGF | S-dC28 | |
| PDGF | 0 | — | 0% |
| PDGF + S-dC2B | 0 | 2 | 60%** |
| S-dC28 + PDGF | 2 | 0 | 79%** |
| S-dC28 + PDGF # | 2 | 0 | 37%* |
| PDGF + S-dC28 § | 0 | 0 | 63%** |

Growth-arrested human aortic SMC were incubated with vehicle alone, PDGF (100 ng/ml) alone, or PDGF (100 ng/ml) in combination with 20 $\mu$M of S-dC28 at 37° C. in a humidified 5% $CO_2$ atmosphere for 48 hours. SMC were then trypsinized and cell numbers immediately determined by triplicate counts with a Coulter Counter. # SMC pre-treated with S-dC28 for 2 hours, followed by three washes with medium and subsequent addition of PDGF. § SMC incubated with PDGF and S-dC28 which had been previously mixed together in a test tube for 2 hours. Values are mean±SD (n=6, * p<0.05, **p<0.01 relative to the PDGF group).

TABLE II

Effects of S-dC28 on bFGF and EGF-Induced SMC Proliferation

| Group | bFGF (ng/ml) | EGF (ng/ml) | S-dC28 ($\mu$M) | Percent Inhibition of SMC Proliferation |
|---|---|---|---|---|
| bFGF | 10 | — | — | 0% |
| bFGF + S-dC28 2 $\mu$M | 10 | — | 2 | 15% |
| bFGF + S-dC28 10 $\mu$M | 10 | — | 10 | 67%** |
| bFGF + S-dC28 20 $\mu$M | 10 | — | 20 | 76%** |
| EGF | — | 10 | — | 0% |
| EGF + S-dC28 2 $\mu$M | — | 10 | 2 | 13% |
| EGF + S-dC28 10 $\mu$M | — | 10 | 10 | 63%** |
| EGF + S-dC28 20 $\mu$M | — | 10 | 20 | 77%** |

Growth-arrested human aortic SMC were incubated with vehicle alone, bFGF (10 ng/ml) alone, or bFGF (10 ng/ml) in combination with various doses of S-dC28 for 48 hours at 37° C. in a humidified 5% $CO_2$ atmosphere. In other experiments, growth-arrested human aortic SMC were incubated with EGF (10 ng/ml) alone, or EGF (10 ng/ml) in combination with various doses of S-dC28 for 48 hours at the same conditions. SMC were then trypsinized and cell numbers immediately determined by triplicate counts with a Coulter Counter. Values are expressed as the percentage of inhibition of bFGF- and EGF-induced SMC proliferation. (**p<0.01 relative to the bFGF alone group or the EGF alone group).

TABLE III

Modulation of the Effects of S-dC28 on SMC
Adhesion by Fibronectin, Laminin and FBS

| Group | S-dC28 ($\mu$M) | SMC Adhesion (% Control) |
|---|---|---|
| Control | 0 | 100 ± 2 |
| Fibronectin + S-dC28 (0.2 $\mu$M) | 0.2 | 84 ± 5 |
| Fibronectin + S-dC28 (2 $\mu$M) | 2 | 81 ± 5 |
| Fibronectin + S-dC28 (20 $\mu$M) | 20 | 73 ± 10** |
| Laminin + S-dC28 (0.2 $\mu$M) | 0.2 | 100 ± 3 |
| Laminin + S-dC28 (2 $\mu$M) | 2 | 103 ± 2 |
| Laminin + S-dC28 (20 $\mu$M) | 20 | 100 ± 3 |
| FBS + S-dC28 (0.2 $\mu$M) | 0.2 | 103 ± 2 |
| FBS + S-dC28 (2 $\mu$M) | 2 | 99 ± 3 |
| FBS + S-dC28 (20 $\mu$M) | 20 | 91 ± 2* |

Tissue culture plates were pre-coated with fibronectin or laminin. Growth-arrested human aortic SMC were incubated with vehicle alone or various doses of S-dC28 in medium 199 containing 0.2% bovine albumin for 2 hours at 37° C. in a humidified 5% $CO_2$ atmosphere. In the case of FBS groups, 5% FBS was added to M199 and the tissue culture plates were not coated. SMC were then trypsinized and cell numbers immediately determined by triplicate counts with a Coulter Counter. Values are means ±SD (n=5). (*p<0.05, **p<0.01 relative to control SMC cultured in media alone).

REFERENCES

1. Nobuyoshi, M., T. Kimura, H. S. Nosaka, S. Moika, K. Ueno, H. Yokui, N. Hamasaki, H. Horiuchi, and H. Ohishi. (1988) *J. Am. Coll. Cardiol.* 12:616–623.
2. Popma, J. J., R. M. Califf, and E. J. Topol. (1991) *Circulation* 84:1426–1436.
3. Liu, M. W., G. S. Roubin, and S. B. King III. (1989) *Circulation* 79:1374–1387.
4. Shi, Y., H. G. Hutchinson, D. J. Hall, and A. Zalewski. (1993) *Circulation* 88:1190–1195.
5. Villa, A. E., L. A. Guzman, E. J. Poptic, V. Labhasetwar, S. D'Souza, C. L. Farrell, E. F. Plow, R. J. Levy, P. E. DiCorleto, and E. J. Topol. (1995) *Circ. Res.* 76:505–513.
6. Stein, C. A., and Y.-C. Cheng. (1993) *Science* 261:1004–1012.
7. Bennett, M. R., S., Anglin, J. R. McEwan, R. Jagoe, A. C. Newby, and G. I. Evan. (1993) *J. Clin. Invest.* 93:820–828.
8. Shi, Y., A. Fard, A. Galeo, H. G. Hutchinson, P. Vernani, G. R. Dodge, D. J. Hall, F. Shaheen, and A. Zalewski. (1994) *Circulation* 90:944–951.
9. Brown, K. E., M. S. Kindy, and G. E. Sonenshein. (1992) *J. Biol. Chem.* 267:4625–4630.
10. Simons, M., and R. D. Rosenberg. (1992) *Circ. Res.* 70:835–843.
11. Ebbecke, M., C. Unterberg, A. Buchwald, S. Stohr, and V. Wiegand. (1992) *Basic Res. Cardiol.* 87:585–591.
12. Biro, S., Y. M. Fu, Z. X. Yu, and S. E. Epstein. (1993) *Proc. Natl. Acad. Sci. U.S.A.* 90:654–658.

13. Simons, M., E. R. Edelman, J.-L DeKeyser, R. Langer, and R. D. Rosenberg. (1992) *Nature* 359:67–70.
14. Burgess, T. L., E. F. Fisher, S. L. Ross, J. V. Bready, Y. -Z. Qian, L. A. Bayewitch, A. M. Cohen, C. J. Herrera, S. S-F. Hu, T. B. Kramer, F. D. Lott, F. H. Martin, G. F. Pierce, L. Simonet, and C. L. Farrell. (1995) *Proc. Natl. Acad. Sci. U.S.A.* 92:4051–4055.
15. Guvakova, M. A., L. A. Yakubov, I. Vlodavsky, J. L. Tonkinson, and C. A. Stein. (1995) *J. Biol. Chem.* 270:2620–2627.
16. Stein, C. A., C. Subasinghe, K. Shinozuka, and J. Cohen. (1988) *Nucl. Acid Res.* 16:3209–3221.
17. Yang, Z., G. Noll, and T. F. Luscher. (1993) *Circulation* 88:832–836.
18. Franke, L., and T. Portmann. (1994) *J. Immunol. Meth.* 171:259–262.
19. Tada, H., O. Shiho, K. Kuroshima, M. Koyamam, and K. Tsukamotok. (1986) *J. Immunol. Meth.* 93:157–165.
20. Ferns, G. A. A., E. W. Raines, K. H. Sprugel, A. S. Montani, M. A. Reidy, and R. Ross. (1991) *Science* 253:1129–1132.
21. Jackson, C. L., and M. A. Reidy. (1992) *Ann. N.Y. Acad. Sci.* 667:141–150.
22. Edelman, E. R., M. A. Nugent, L. T. Smith, and M. T. Karnovsky. (1992) *J. Clin. Invest.* 89:465–473.
23. Clowes, A. W., M. A. Reidy, and M. M. Clowes. (1983) *Lab. Invest.* 49:327–333.
24. Edelman, E. R., D. H. Adams, and M. S. Karnovsky. (1990) *Proc. Natl. Acad. Sci. U.S.A.* 87:3773–3777.
25. Jackson, C. L., E. W. Raines, R. Ross, and M. A. Reidy. (1993) *Arterioscler. Thromb.* 13:1218–1226.
26. Lindner, V., D. A. Lappi, A. Baird, R. A. Majack, and M. A. Reidy. (1991) *Circ. Res.* 68:106–113.
27. Soto, Y., R. Hamanaka, J. Ono, M. Kuwano, D. B. Rifkin, and R. Takaki. (1991) *Biochem. Biophys. Res. Commun.* 174:1260–1266.
28. Lindner, V., and M. A. Reidy. (1991) *Proc. Natl. Acad. Sci. U.S.A.* 88:3739–3743.
29. Hansson, G. K., L. Jonasson, J. Holm, M. M. Clowes, and A. W. Clowes. (1988) *Circ. Res.* 63:712–719.
30. Hansson, G. K., M. Hellstrand, L. Rymo, L. Rubbia, and G. Gabbiani. (1989) *J. Exp. Med.* 170:1595–1608.
31. Hansson, G. K., and J. Holm. (1991) *Circulation* 84:1266–1272.
32. Wang, W. Z., H. J. Chen, K. N. Giedd, A. Schwartz, P. J. Cannon, and L. E. Rabbani (1995) *Circ. Res.* in press.
33. Morishita, R., G. H. Gibbons, K. E. Ellison, M. Nakajima, L. Zhang, Y. Kareda, T. Ogihara, and V. J. Dzau (1993) *Proc. Natl. Acad. Sci. U.S.A.* 90:8474–8478.
34. Morishita, R., G. H. Gibbons, K. E. Ellison, M. Nakajima, H. von der Leyen, L. Zhang, Y. Kareda, T. Ogihara, and V. J. Dzau (1994) *J. Clin. Invest.* 93:1458–1464.
35. Abe, J., W. Zhou, J. Taguchi, N. Takuwa, K. Miki, H. Okazaki, K. Kurokawa, M. Kumada, and Y. Takuwa. (1994) *Biochem. Biophys. Res. Commun.* 198:16–24.
36. Simons, M., E. R. Edelman, and R. D. Rosenberg. (1994) *J. Clin. Invest.* 93:2351–2356.
37. Beaucage, S., and Caruthers, M., (1981) *Tetrahedron Lett.* 37:3557.
38. Ghosh, S., et al. (1990) *J. Biol. Chem.* 265:2935–1940.
39. Hemken, P., et al. (1992) *J. Biol. Chem.* 267:9948–9957.
40. Iversen, P. (1991) *Anti-Cancer Drug Des.* 6:531.
41. Lestinger, R., U.S. Pat. No. 4,958,013, issued Sep. 18, 1990; Rosenberg, P., et al. PCT International Application No. PCT/US92/05305, filed Jun. 23, 1992; Maggi, A, and Nicolin, A., PCT International Application No. PCT/EP92/01745, filed Jul. 29, 1992.
42. Ratajczak, et al. (1992) *Proc. Natl. Acad. Sci. U.S.A.* 89:11823.
43. Shewmaker et al., U.S. Pat. No. 5,107,065, issued Apr. 21, 1992.
44. Stein, C., et al. (1991) *Pharmac. Ther.* 52:365–384.
45. Stein, C., et al. (1993) *Biochemistry* 32:4855–4861.
46. Stein, C. A., and Cheng, Y.,-C., (1993) *Science:* 1004–1012.
47. Tullis, U.S. Pat. No. , issued Jun. 11, 1991.
48. Uhlmann, E., and Peyman, A. (1990) *Chem. Rev.* 90:544–579.
49. Zhao, Qiuyan, et al. (1993) *Antisense Research and Development* 3:53–66.
50. Ross, R., et al.,(1974) *Proc. Natl. Acad. Sci. USA* 71:1207–1210.
51. Raines, E. W. and Ross, R. (1982) *J. Biol. Chem.* 257:5154–5160.
52. Gao, W. Y., et al., (1992) *Mol. Pharm.* 43:45–50.
53. Khaled, Z., et al., (1996) *Nucleic Acids Res.* 24:737–745.
54. Engel, J., (1992) *Biochemistry.* 31:10643–10651.
55. Benimetskaya, L., et al., (1995) *Nucleic Acids Res.* 23:4239–4245.
56. Dean, N. M., et al., (1994) *J. Biol. Chem.* 269:16416–16424.
57. Khaled, Z., et al., (1995) *Clin. Cancer Res.* 1:113–122.
58. Stein, C. A., et al., (1993) *Cancer Res.* 53:2239–2248.
59. Nakajima, M., et al, (1991) *J. Biol. Chem.* 266:9661–9666.
60. Bachinsky, W. B., et al., (1995) *J. Clin. Invest.* 96:2583–2592.

What is claimed is:

1. A method of inhibiting neointimal formation after balloon injury in a subject which comprises administering to the subject an amount of a phosphorothioate oligonucleotide moiety effective to inhibit neointimal formation, wherein the phosphorothioate oligonucleotide moiety lacks a contiguous G-guartet residue.

2. The method of claim 1, wherein the phosphorothioate oligonucleotide moiety comprises a phosphorothioate oligonucleotide.

3. The method of claim 2, wherein the phosphorothioate oligonucleotide is a homopolymer.

4. The method of claim 2, wherein the phosphorothioate oligonucleotide is a heteropolymer.

5. The method of claim 2, wherein the phosphorothioate oligonucleotide is stereo regular.

6. The method of claim 2, wherein the phosphorothioate oligonucleotide is stereo non-regular.

7. The method of claim 2, wherein the phosphorothioate oligonucleotide is stereo random.

8. The method of claim 1, wherein the phosphorothioate oligonucleotide moiety comprises a phosphorothioate oligonucleotide linked to a cholesteryl moiety.

9. The method of claim 1, wherein the phosphorothioate oligonucleotide moiety comprises a phosphorothioate oligonucleotide linked to an intercalating agent, a cross-linker, an artificial endonuclease, a lipophilic carrier, a peptide conjugate, or a combination thereof.

10. The method of claim 2, wherein the phosphorothioate oligonucleotide has a length of from about 18 to about 100 nucleotide residues.

11. The method of claim 1, wherein the phosphorothioate oligonucleotide moiety comprises a phosphorothioate oligonucleotide conjugated to a sulfated carbohydrate.

12. The method of claim 1, wherein the phosphorothioate oligonucleotide moiety comprises a phosphorothioate oligonucleotide conjugated to a carbohydrate or glycan.

13. The method of claim 1, wherein administering to the subject is oral, intravenous, intramuscular, intratracheal or subcutaneous.

14. The method of claim 1, wherein the phosphorothioate oligonucleotide moiety is SdC28.

15. A pharmaceutical composition comprising a phosphorothioate oligonucleotide moiety in an amount effective to inhibit neointimal formation after balloon injury and a pharmaceutically acceptable carrier, wherein the phosphorothioate oligonucleotide moiety lacks a contiguous G-qguartet residue.

* * * * *